(12) United States Patent
Duan

(10) Patent No.: US 10,221,420 B2
(45) Date of Patent: Mar. 5, 2019

(54) APTAMER CONSTRUCT

(71) Applicant: DEAKIN UNIVERSITY, Victoria (AU)

(72) Inventor: Wei Duan, Victoria (AU)

(73) Assignee: DEAKIN UNIVERSITY (AU)

( * ) Notice: Subject to any disclaimer, the term of this patent is extended or adjusted under 35 U.S.C. 154(b) by 0 days.

(21) Appl. No.: 15/117,164

(22) PCT Filed: Feb. 5, 2015

(86) PCT No.: PCT/AU2015/050039
§ 371 (c)(1),
(2) Date: Aug. 5, 2016

(87) PCT Pub. No.: WO2015/117201
PCT Pub. Date: Aug. 13, 2015

(65) Prior Publication Data
US 2016/0355820 A1     Dec. 8, 2016

(30) Foreign Application Priority Data

Feb. 5, 2014 (AU) .............................. 2014900347

(51) Int. Cl.
| | | |
|---|---|---|
| A61K 48/00 | (2006.01) | |
| C07H 21/02 | (2006.01) | |
| C07H 21/04 | (2006.01) | |
| C12N 15/115 | (2010.01) | |
| C12Q 1/6886 | (2018.01) | |
| G01N 33/574 | (2006.01) | |
| A61K 31/704 | (2006.01) | |
| A61K 47/48 | (2006.01) | |
| G01N 33/53 | (2006.01) | |

(52) U.S. Cl.
CPC .......... *C12N 15/115* (2013.01); *A61K 31/704* (2013.01); *A61K 47/48092* (2013.01); *C12Q 1/6886* (2013.01); *G01N 33/5308* (2013.01); *G01N 33/574* (2013.01); *G01N 33/57492* (2013.01); *C12N 2310/16* (2013.01); *C12N 2310/315* (2013.01); *C12N 2310/317* (2013.01); *C12N 2310/322* (2013.01); *C12N 2310/3341* (2013.01); *C12N 2310/3511* (2013.01); *C12N 2310/3517* (2013.01); *G01N 2333/70596* (2013.01)

(58) Field of Classification Search
CPC .............................. C12N 15/115; C12N 15/111
See application file for complete search history.

(56) References Cited

U.S. PATENT DOCUMENTS

| | | |
|---|---|---|
| 5,270,163 A | 12/1993 | Gold et al. |
| 5,475,096 A | 12/1995 | Gold et al. |
| 5,637,459 A | 6/1997 | Burke et al. |
| 7,998,940 B2 | 8/2011 | Diener et al. |
| 9,840,712 B2 | 12/2017 | Duan |
| 2007/0050146 A1 | 3/2007 | Bentwich et al. |
| 2009/0047295 A1 | 2/2009 | Berry et al. |
| 2009/0269356 A1* | 10/2009 | Epstein et al. ....... C12N 15/113 |
| 2011/0206614 A1 | 8/2011 | McAllister et al. |

FOREIGN PATENT DOCUMENTS

| | | |
|---|---|---|
| JP | 2007319153 A | 12/2007 |
| WO | 0056930 | 9/2000 |
| WO | 2003066097 A2 | 8/2003 |
| WO | 2004084950 A2 | 10/2004 |
| WO | 2006051405 A2 | 5/2006 |
| WO | 2007137117 A2 | 11/2007 |
| WO | 2014019024 A1 | 2/2014 |

OTHER PUBLICATIONS

Bagalkot et al., "An aptamer-doxorubicin physical conjugate as a novel targeted drug-delivery platform", Angew. Chem. Int. Ed. vol. 45, pp. 1-5, 2006, 6 Pages.
Shigdar et al., "Aptamers as theranostic agents: modification, serum stability and functionalisation", Sensors. vol. 13, pp. 13624-13637, doi:10.3390/s131013624, 2013, 14 Pages.
Shigdar et al., "RNA aptamers targeting cancer stem cell marker CD133", Cancer Letters vol. 330, 2013, pp. 84-95.
Wang et al., "Improving the stability of aptamers by chemical modification", Curr. Med. Chem. vol. 18, pp. 4126-4138, 2011, 14 Pages.
Examination Report for New Zealand Patent Application No. 704719, dated Sep. 15, 2017 (5 pages).
Ray et al., "Aptamers for Targeted Drug Delivery," Pharmaceuticals, May 27, 2010, pp. 1761-1778, vol. 3.
International Search Report and Written Opinion of the International Searching Authority for International Application No. PCT/AU2013/000850, dated Sep. 26, 2013 (39 pages).
Cerchia et al., "Nucleic acid aptamers in cancer medicine," FEBS Letters, 2002, pp. 12-16, vol. 528.
Extended European Search Report for European Patent Application No. 13825421.4, dated Mar. 7, 2016 (11 pages).
Ferrandina et al., "Targeting CD133 Antigen in Cancer", Expert Opinion on Therapeutic Targets, Jun. 17, 2009, pp. 823-837, vol. 13, No. 7.
Kanwar et al., "Chimeric aptamers in cancer cell-targeted drug delivery," Critical Reviews in Biochemistry and Molecular Biology, 2011, pp. 459-477, vol. 46, No. 6.
Karaballi et al., "Development of an electrochemical surface-enhanced Raman spectroscopy (EC-SERS) aptasensor for direct detection of DNA hybridization," Phys Chem Chem Phys, Mar. 2, 2015, pp. 21356-21363, vol. 17.
Yin et al., "AC133, a Novel Marker for Human Hematopoietic Stem and Progenitor Cells," Blood, Dec. 15, 1997, pp. 5002-5012, vol. 90, No. 12.

* cited by examiner

*Primary Examiner* — Amy H Bowman
(74) *Attorney, Agent, or Firm* — Dorsey & Whitney LLP

(57) ABSTRACT

The present disclosure relates to aptamers and uses thereof, in particular, aptamers which specifically bind to CD133 and which are particularly useful in the diagnosis and/or treatment of cancer.

20 Claims, 12 Drawing Sheets
Specification includes a Sequence Listing.

APTAMER CONSTRUCT

RELATED APPLICATIONS AND INCORPORATION BY REFERENCE

The present application is a Section 371 National Stage Application of International Application No. PCT/AU2015/050039, filed on Feb. 5, 2015, which claims priority to Australian Application No. 2014900347, filed on Feb. 5, 2014, both of which are hereby incorporated by reference in their entirety.

All documents cited or referenced herein, together with any manufacturer's instructions, descriptions, product specifications and product sheets for any products mentioned herein or any document incorporated by reference herein, are hereby incorporated herein by reference in their entirety.

This application claims priority from AU 2014900347 entitled 'Aptamer construct' filed 5 Feb. 2014.

SEQUENCE LISTING

A sequence listing submitted in computer readable format is hereby incorporated by reference. The computer readable file is named P261208WOUS01_SequenceListing.txt and contains 4.0 kilobytes.

FIELD OF THE INVENTION

The present disclosure relates to aptamers and uses thereof, in particular, aptamers which specifically bind to CD133 and which are particularly useful in the diagnosis and/or treatment of cancer.

BACKGROUND OF THE INVENTION

CD133, also known as Prominin-1 is a pentaspan, highly glycosylated, membrane glycoprotein that is associated with cholesterol in the plasma membrane. Though this protein is known to define a broad population of cells, including somatic stem and progenitor cells, and is expressed in various developing epithelial and differentiated cells, its exact function is still being elucidated. It has however been linked to the Notch-signalling pathway which is critical for binary cell fate, differentiation of intestinal epithelium, and lymphopoiesis (Ulasov et al. 2011. Mol Med 17:103-12). More interest has been shown in this molecule in recent years due to it being thought to be a marker of cancer stem cells (CSCs) in a number of cancers. Indeed, growing evidence has shown that CD133 is expressed on CSCs in a number of cancers, and there is an enhanced tumorigenic potential of CD133+ cells versus their negative counterparts in immunodeficient mice (Dittfeld et al. 2009. Radiother Oncol 92:353-61).

Immunotherapy has had a great impact on the treatment of cancer in recent years. However, the use of antibodies, even humanised antibodies, can lead to adverse side effects that can be fatal (Hansel et al. 2010. Nat Rev Drug Discov 9:325-38). This has led to the search for 'bigger and better' options. There have been several attempts made to use nucleic acids as therapeutics though these have met with disappointing results, not least because of the failure of these nucleic acids to enter the cell (Shigdar et al. 2011. Br J Haematol 155:3-13).

Chemical antibodies, termed aptamers, have been increasingly utilised for clinical applications in the last twenty years. Indeed, one aptamer, pegaptanib (an anti-VEGF aptamer) has been approved by the FDA and several more are in clinical trials. Increased interest in the use of aptamers for therapy is due to several reasons, including the fact that they exhibit no immunogenicity, little batch-to-batch variation due to being chemically synthesized, and are more stable than conventional antibodies. Due to their small size, they also show superior tumour penetration. However, their most important feature is the ability to attach these aptamers to nanoparticles, drugs, imaging agents or other nucleic acid therapeutics without loss-of-function (Meng et al. 2012. PLoS One 7:e33434). This functionalisation is leading to new and more targeted therapies, with fewer side effects than current treatment modalities (Meng et al. 2012 supra). When compared to conventional treatment which is largely a passive process, targeted delivery systems are much more effective. For an aptamer to be an effective drug delivery agent, the aptamer must bind to its target on the cell surface and be internalised within a short period of time. Accordingly there is a need in the art for aptamers with improved binding characteristics and tumor penetration

SUMMARY OF THE INVENTION

It has recently been appreciated that cancer stem cells are responsible for the formation and growth of neoplastic tissue and are naturally resistant to chemotherapy, explaining why traditional chemotherapies can initially shrink a tumour but fail to eradicate it in full, resulting in eventual recurrence. According to the cancer stem cell hypothesis, CD133-positive cells (CD 133+) determine long-term tumour growth and, therefore are suspected to influence clinical outcome. It has been recently found that both the proportion of CD133-positive cells and their topological organisation in clusters were significant prognostic factors for adverse progression-free survival and overall survival independent of tumour grade, extent of resection, or patient age.

Current techniques for targeting of CD133-positive cancer stem cells use conventional antibody-based systems, but lack sensitivity due to the size of the anti-CD133 antibodies available and their relative inability to penetrate tissues.

Accordingly, the generation of aptamers to CD133+ cells would be advantageous in the eradication of cancer. This has been addressed by the present inventor who has generated aptamers specific for CD133 which are rapidly internalised and show superior tumour penetration. In particular, the aptamers of the present disclosure are particularly effective theranostic agents.

The present disclosure provides an aptamer which binds specifically to CD133. In one example, the aptamer is an oligonucleotide. In one example, the oligonucleotide may be RNA, DNA or a hybrid RNA/DNA aptamer and/or may comprise nucleotides other than adenine, cytosine, guanine, thymine and uracil.

The present disclosure also provides an aptamer comprising the sequence 5'-X-ACGUAUACUAU-Y-3' (SEQ ID NO:1), wherein the sequence of X and Y are complementary so as to be capable of base pairing and wherein X and Y individually comprise a length of CG paired nucleotides sufficient to permit attachment of at least one moiety thereto.

According to the aptamer of the present disclosure, X and Y may individually comprise at least 4 CG paired nucleotides (4 CG pairs). In another example, X and Y may individually comprise at least 5 CG paired nucleotides, or at least 6 CG paired nucleotides, or at least 7 CG paired nucleotides, or at least 8 CG paired nucleotides, or at least 9 CG paired nucleotides, or at least 10 CG paired nucleotides, or at least 11 CG paired nucleotides, or at least 12 CG paired nucleotides, or at least 13 CG paired nucleotides, or at least 14 CG paired nucleotides, or at least 15 CG paired nucleotides.

In another example, the aptamer may comprise between 4 and 15 CG paired nucleotides (4-15 CG pairs). In another example, the aptamer may comprise between 2 and 12 CG paired nucleotides. In another example, the aptamer may comprise between 2 and 10 paired nucleotides, between 2 and 8 paired nucleotides, or between 2 and 6 paired nucleotides.

It will be appreciated by persons skilled in the art that the CG paired nucleotides comprise the stem region of the aptamer.

In one example, the aptamer exhibits an equilibrium dissociation constant ($K_D$) for CD133 of about 24 nM or less. In another example, the aptamer exhibits a dissociation constant ($K_D$) for CD133 of about 24 nM. In another example, the aptamer exhibits a dissociation constant ($K_D$) for CD133 of 24 nM. In another example, the dissociation constant is determined by measuring the binding of the aptamer to CD133 expressed on HT29 cells.

In one example, the aptamer is a hybrid RNA/DNA apatmer. In another example, the aptamer is an isolated apatmer. In another example, the aptamer is synthesised according to art known methods (e.g. SELEX).

In one example, the aptamer according to the present disclosure specifically binds to CD133. In another example, the aptamer according to the present disclosure selectively binds to CD133.

In one example, the aptamer comprises the sequence (SEQ ID NO: 2)
5'-CGCGCGCCGC<u>ACGUAUACUAU</u>GCGGCGCGCG-3'.

In one example, the aptamer comprises the sequence according to SEQ ID NO:2 wherein the sequence comprises 10 GC paired nucleotides which are DNA. In yet a further example, the aptamer comprises the sequence 5'-ACGUAUACUAU-3' (SEQ ID NO:3) which is RNA. In yet another example, the aptamer comprises the sequence according to SEQ ID NO:2 comprising the sequence according to SEQ ID NO:3 wherein SEQ ID NO:3 is RNA and the remaining sequence is DNA. In one example, the stem region is that of the predicted two dimensional structure of the aptamer shown in FIG. 1.

In one example, the aptamer consists essentially of the sequence according to SEQ ID NO:2. The aptamer may alternatively consist of the sequence according to SEQ ID NO:2. The aptamer according to the present disclosure or according to SEQ ID NO:2 may include additional sequences. The aptamer according to the present disclosure may comprise a sequence having at least 95% identity to SEQ ID NO:2, or at least 90% identity, at least 92% identity, at least 85% identity, at least 80% identity, at least 75% identity, or at least 70% identity.

In one example, attachment of the moiety is by intercalation. In another example, the attachment is by conjugation. In another example, the attachment is by electrostatic binding. In another example, the attachment is via a linker.

The moiety according to the present disclosure may be a DNA stain or a molecule used in chemotherapeutic treatment or a molecule which is capable of performing both functions. Examples of suitable molecules that are capable of intercalating into the aptamer according to the present disclosure may be selected from doxorubicin, adriamycine, berberine, provflavine, mitoxantrone, daunorubicin, thalidomide, dactinomycin, danomycin, actinomycin D, 9-aminoacridine, amrubicin, amsacrine, anthramycine, berbine, bleomycin, elliplicine, epirubicin, idarubicin, methpyrillo, mithramycin, mitomycin, mitomycin C, mitoxantrone, mitoxantrone, pirarubicin, pixantrone, plicamycin, proflavine, prodigiosin, thalidomide, voreloxin, valrubicin, zorubicin. chlorpheniramine, prodisiosin, methapyrillino, mitomycin, distamycin, dantinomycin, distamycin, carboplatin, cisplatin and other platinum derivatives, Hoechst 33258, berenil, DAPI or carcinogenic agents (including the exo 8,9 epoxide of aflatoxin B1, acridines such as proflavine or quinacrine or ethidium bromide). Other GC intercalating agents will be familiar to persons skilled in the art of the present invention and are intended to be included within the scope of the present disclosure. In a preferred example, the molecule is doxorubicin (DOX).

The sequences of X and Y are capable of forming a base pair thus providing the stem region of the aptamer. Without wishing to be bound by theory, the moiety is preferably capable of attaching to the aptamer of the present disclosure by intercalating between CpG sites in the base paired X and Y DNA sequences. With respect to DOX, on average there are about 2.5 molecules of DOX for every CpG sites or put another way, about 2.5 molecules of DOX that are capable of intercalating into the sequence according to SEQ ID NO:2.

The total length of the aptamer may be between 19 and 101 nucleotides, between 21 and 85 nucleotides, between 25 and 75 nucleotides, between 31 and 65 nucleotides, between 41 and 55 nucleotides, or between 31 and 41 nucleotides. It will be appreciated by persons skilled in the art that while the present disclosure describes aptamers comprising at least 15 CG paired nucleotides, the remaining stem sequence may comprise RNA or DNA sequence other than alternating CG paired nucleotides The aptamer of the present disclosure may further comprise one or more nucleotide substitutions within the sequence which maintain the binding loop of the aptamer. In one example, the sequence comprises at least one, two, three, four, five or six substitutions within the stem region of the aptamer disclosed herein or within the aptamer sequence according to SEQ ID NO:1 or SEQ ID NO:2. It will be appreciated that the number of substitutions will depend upon the length of the aptamer and will be tolerated to the extent that the aptamer is still capable of permitting attachment of a molecule such as doxorubicin.

In one example, the aptamer further comprises one or more modifications that improve aptamer stability (in vitro and/or in vivo). In one example, the pyrimidine nucleotide bases (C and/or U) in the loop region are 2'-fluoro (2'-F) modified. For the avoidance of doubt the loop region is the sequence 5'-ACGUAUACUAU-3' (SEQ ID NO:3). In a further example, the C base in the aptamer stem region (deoxyCytidine, dC) is modified to a 5-methyl deoxyCytidine (5-methyl dC). When dC is substituted for 5-methyl dC, the Tm of the aptamer may increase by as much as 0.5° C. per insertion. Without wishing to be bound by theory, the presence of 5-methyl dC in CpG motifs can prevent or limit unwarranted immune responses that otherwise occur of oligonucleotides are administered in vivo, which is of particular importance for in vivo diagnostics and therapeutics. In another example, the 3' end of the aptamer may be modified to protect it from nuclease digestion. In another example, aptamer is modified by modifying the 3' terminus with a phosphate group, a phosphate ester or an inverted dT (invdT-3'). In another example, the 5' end may be coupled to a dye such as biotin, fluorescein isothiocyanate (FITC), cyanine (Cy3 or Cy5). Additional modifications will be familiar to persons skilled in the art and are considered to be encompassed by the present disclosure.

In one example, the present disclosure provides a hybrid RNA/DNA aptamer comprising the sequence 5'-X-A(2'fC)G(2'-fU)A(2'fU)A(2'fC)(2'fU)A(2'fU)-Y-(inv dT)-3' (SEQ ID NO:4) wherein X and Y are complementary so as to be capable of base pairing and wherein X and Y individually comprise a length of CG paired nucleotides, f=2'-fluoro and inv dT=an inverted dT (reverse linkage) and wherein the length of X and Y is sufficient to permit the attachment of at least one moiety thereto. In a particular example, X and Y are DNA.

In one example, the present disclosure provides a hybrid RNA/DNA aptamer comprising the sequence 5'-mCGmCG-mCGmCmCGmCA(2'fC)G(2'-fU)A(2'fU)A(2'fC)(2'fU)A(2'fU)GmCGGmCGmCGmCG-(inv dT)-3' (SEQ ID NO:5), wherein C=5-methyl dC, f=2'-fluoro and inv dT=an inverted dT (reverse linkage). According to this example, the aptamer comprises a 3' terminal G which is inverted.

In another example, the hybrid RNA/DNA aptamer consists essentially of the sequence according to SEQ ID NO:4 or SEQ ID NO:5. In another example, the hybrid RNA/DNA aptamer consists of the sequence according to SEQ ID NO:4 or SEQ ID NO:5.

The aptamer according to the present disclosure may comprise a sequence having at least 95% identity to SEQ ID NO:4 or 5, or at least 90% identity, at least 92% identity, at least 85% identity, at least 80% identity, at least 75% identity, or at least 70% identity to the sequence of SEQ ID NO:4 or 5.

The aptamer may further comprise a 3' or 5' dye such as Cy3 or Cy5.

Methods of preparing 2'-fluoro modified RNA bases are known in the art. In one example, the 2'-fluro modified bases are incorporated directly during the synthesis of an RNA transcript.

The present disclosure also provides an aptamer having substantially the same ability to bind to CD133 as that of an aptamer comprising a sequence of SEQ ID NO:1, SEQ ID NO:2, SEQ ID NO:4 or SEQ ID NO:5.

In one example, the aptamer according to the present disclosure specifically binds to CD133$^+$ cell(s). In another example, the aptamer according to the present disclosure selectively binds to CD133$^+$ cell(s). The CD133+ cell(s) may be stem cell(s). The stem cell may be a purified or isolated stem cell and in one example may be a cancer stem cell. In an example, the cancer stem cell(s) is characterised as (i) expressing CD133, (ii) is tumorigenic, (iii) is capable of self renewal (iv) is capable of differentiating and (v) resistant to apoptosis by conventional therapy.

The cancer stem cells may be alternatively described as isolated, enriched or purified from a source, such as a biological sample. In another example, the cancer stem cell(s) represent a population of cells enriched on the basis of CD133$^+$ expression. In another example, the population of cells comprises at least 30%, 40%, 50%, 60%, 70%, 80%, 90% or 95% cancer stem cells.

In one example, the CD133 expressing cells and/or cancer stem cells are in vivo. In another example, the CD133 expressing cells and/or cancer stem cells are in vitro. In a further example, the C133 expressing cells and/or cancer stem cells are present in a biological sample obtained from a subject. The binding of the aptamer may be detected in any convenient manner, for example, by detecting a label associated with the aptamer, by imaging the aptamer or by determining the amount of bound aptamer. Suitable methods are described for example in WO 2004/081574.

In another example, the CD133 expressing cells and/or cancer stem cells of the present disclosure may express one or more markers individually or collectively selected from the group consisting of CD44, ABCG2, β-catenin, CD117, ALDH, VLA-2, CD166, CD201, IGFR, EpCAM, and EGF1R.

By "individually" is meant that the disclosure encompasses the recited markers or groups of markers separately, and that, notwithstanding that individual markers or groups of markers may not be separately listed herein the accompanying claims may define such marker or groups of markers separately and divisibly from each other.

By "collectively" is meant that the disclosure encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

In another example, the cancer stem cell according to the present disclosure is a brain cancer stem cell, a metastatic brain cancer cell, a breast cancer stem cell, a prostate cancer stem cell, a pancreatic cancer stem cell, a colon cancer stem cell, a liver cancer stem cell, a lung cancer stem cell, an ovarian cancer stem cell, a skin cancer stem cell or a melanoma stem cell.

The aptamer of the present disclosure may be used in treatment or diagnosis. Furthermore, because DOX is naturally fluorescent it can be used simultaneously for therapy and diagnosis (i.e. as a theranostic).

The present disclosure also provides a diagnostic or theranostic agent comprising an aptamer according to the present disclosure. In one example, the aptamer is the aptamer according to SEQ ID NO:1, SEQ ID NO:2, SEQ ID NO:4 or SEQ ID NO:5. In another example, the diagnostic agent comprises the aptamer of the present disclosure coupled to a detectable label. In one example, the diagnostic agent is used to detect for CD133 expressing cancer stem cells in vivo or in vitro. In one example, the theranostic is an aptamer-Dox conjugate.

The present disclosure also provides a method for identifying or detecting a CD133 expressing cell(s) and/or cancer stem cell(s) in a subject or a biological sample obtained from a subject, having, or suspected of having cancer, the method comprising contacting the cell(s) with a diagnostic agent or theranostic agent as described herein.

In one example, the diagnostic or theranostic agent of the present disclosure can be used to detect the presence of CD133 expressing cells and/or cancer stem cells in a subject or in a biological sample obtained from a subject having a tumour or suspected of having a tumour. If required, detection can be facilitated by coupling the aptamer to a detectable label. Examples of detectable labels include various enzymes, prosthetic groups, fluorescent materials, luminescent materials, bioluminescent materials, electron dense labels, labels for MRI and radioactive materials.

The present disclosure also provides the aptamer as described herein or the diagnostic agent as described herein for use in histological examination of biological samples. Methods for preparing histological samples will be familiar to persons skilled in the art.

The aptamer of the present disclosure may be further coupled to a moiety which may be an active moiety. The moiety may be a ligand, such as a further aptamer or an alternative ligand. The moiety may be an immunoglobulin, or fragment or portion of an immunoglobulin, a therapeutic agent, another drug or bioactive agent, toxin, or radionuclide. Alternatively, the moiety may include siRNA, DNAzymes or ribozymes. Combinations of any of the foregoing moieties are also included in the present disclosure.

The present disclosure also provides an expression vector encoding the aptamer as described herein. Also provided are nucleotide sequences complementary to any one of SEQ ID NO:1 to SEQ ID NO:5, in particular complementary to any one of SEQ ID NO:1 to SEQ ID NO:5.

The present disclosure also provides a method for treating cancer in a subject in need thereof, comprising providing a subject with the aptamer, or theranostic agent as described herein. The subject being treated is typically one which would benefit from treatment with the aptamer or theranostic of the present disclosure. In one example, the subject is diagnosed as having cancer. Alternatively, the subject is one which is suspected of having cancer in which case it may be appropriate to administer the theranostic agent to the subject. The aptamer of the present disclosure which is couple to a moiety as described herein, or the theranostic agent as described herein may be administered to the subject over a period of weeks, months or years to monitor and/or treat the subject.

The subject according to the present disclosure may be one which has, or is suspected of having a cancer selected from brain cancer, breast cancer, prostate cancer, pancreatic cancer, colon cancer, liver cancer, lung cancer, ovarian cancer, skin cancer, melanoma or any other cancer in which CD133+ cells are present. In one example, the cancer is any cancer in which CD133 expressing cells and/or cancer stem cells are present or suspected of being present.

The present disclosure also provides the use of an aptamer as described herein in the manufacture of a diagnostic reagent for the detection or diagnosis of cancer.

The present disclosure also provides use of an aptamer according to the present disclosure or the theranostic agent according to the present disclosure in the manufacture of a medicament for treating cancer in a subject.

The present disclosure also provides use of an aptamer according to the present disclosure or the theranostic agent according to the present disclosure in medicine.

The present disclosure also provides use of an aptamer according to the present disclosure or the theranostic agent according to the present disclosure for treating cancer in a subject.

The present disclosure also provides a composition comprising a therapeutically effective amount of an aptamer, or theranostic agent according to the present disclosure, together with a pharmaceutically acceptable carrier and/or excipient. In one example, the composition is a pharmaceutical composition.

The aptamer, theranostic agent or composition as described herein may be used alone or in combination with other treatment modalities. For example, the aptamer or pharmaceutical composition may be used in combination with radiotherapy or other chemotherapy agents. While not wishing to be bound by theory, it is postulated that the radiotherapeutic and/or chemotherapeutic agents can be used to shrink tumours by primarily targeting rapidly dividing cells which are typically the progeny cells of the cancer stem cells. The aptamer, theranostic agent or composition described herein can then be administered to the site of the tumour to specifically deplete cancer stem cells. Accordingly, the aptamer theranostic agent or composition described herein can be used together with radiotherapy or chemotherapy or subsequent to chemotherapy or radiotherapy treatment. Furthermore, the aptamer, theranostic agent or composition described herein can be used post-surgical resection of the tumour to eliminate any remaining cancer cells that may have remained following surgery.

In another example, the aptamer is provided on the surface of a liposome. The liposome may contain a drug. Examples of suitable drugs include chemotherapeutic agents, immune checkpoint inhibitors (e.g. PD-1), antibiotics, immunoglobulins or antibodies, steroids, or pain medications.

The aptamer or composition comprising the aptamer can be administered to the subject by methods known in the art. In one example, the aptamer or composition is administered parenterally, for example by intravenous, intramuscular, hypodermic, or local injection).

It is also contemplated that the aptamer, theranostic agent or composition described herein can be combined with one or more additional aptamers which target an antigen present on a cancer stem cell.

Each example of the disclosure shall be taken to apply mutatis mutandis to a method for treating, preventing or ameliorating cancer in a subject.

Positive CD133 Aptamer-Dox conjugate, (B) the negative control CD133 Aptamer-Dox conjugate has an identical nucleic acid sequence as the positive aptamer with the exception of a 2'-O-methyl modification instead of a 2'-fluoro chemical modification resulting in an altered 3-D structure that abolishes its binding to CD133, and (C) Positive CD133 Aptamer unconjugated.

Figure 8:
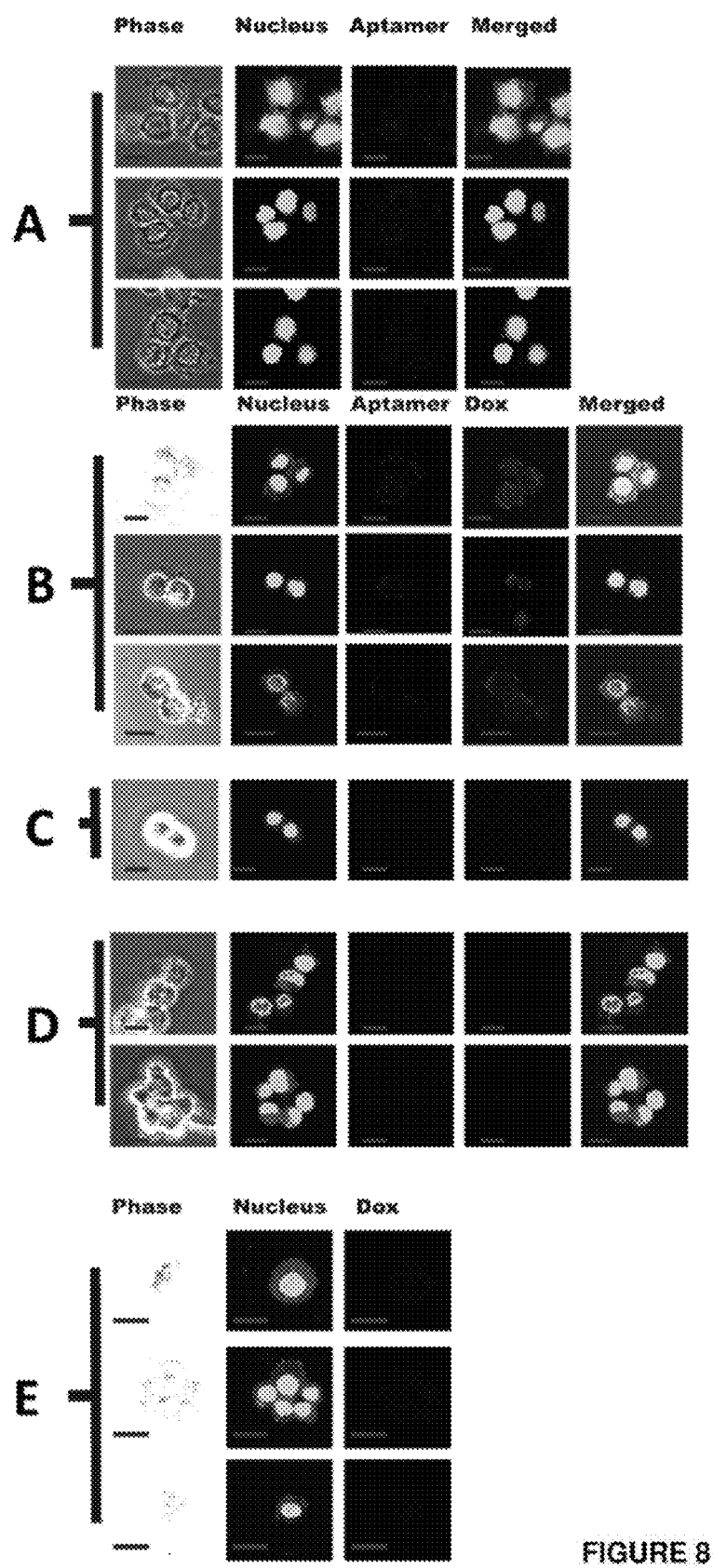

FIG. 8. Confocal microscopy of internalised DOX and aptamer. (A-C) Positive CD133 HT29 cell line. (A) CD133 Aptamer. (B) CD133 aptamer-Dox conjugate. (C) Negative control aptamer-Dox conjugate. (D) Negative control cell line HEK293T incubated with CD133 aptamer-Dox conjugate. (E) HT29 Cell line incubated with free DOX. Scale bar=20 μm.

Figure 9:
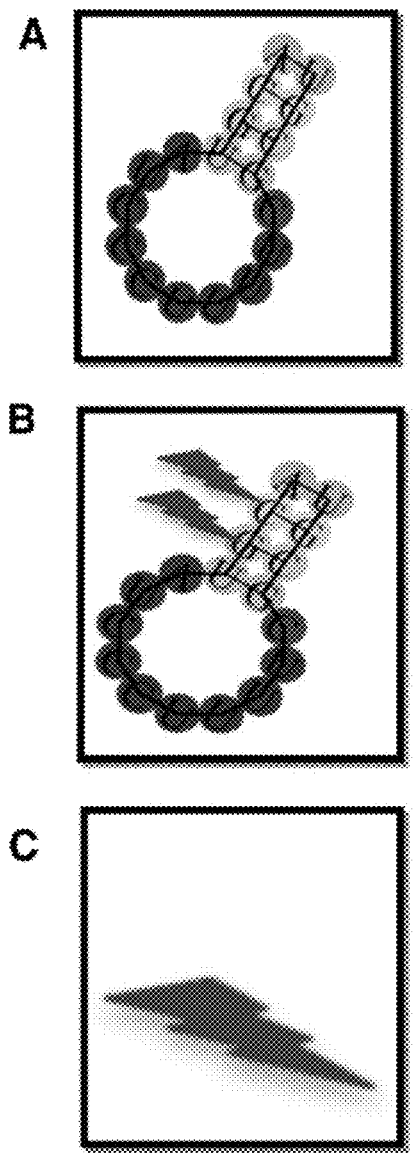

FIG. 9. Treatments for the confocal microscopy assessment of internalization of DOX and aptamer: (a) CD133 Aptamer, (b) CD133 Aptamer-Dox conjugate, and (c) negative control incubated with free DOX.

Figure 10:
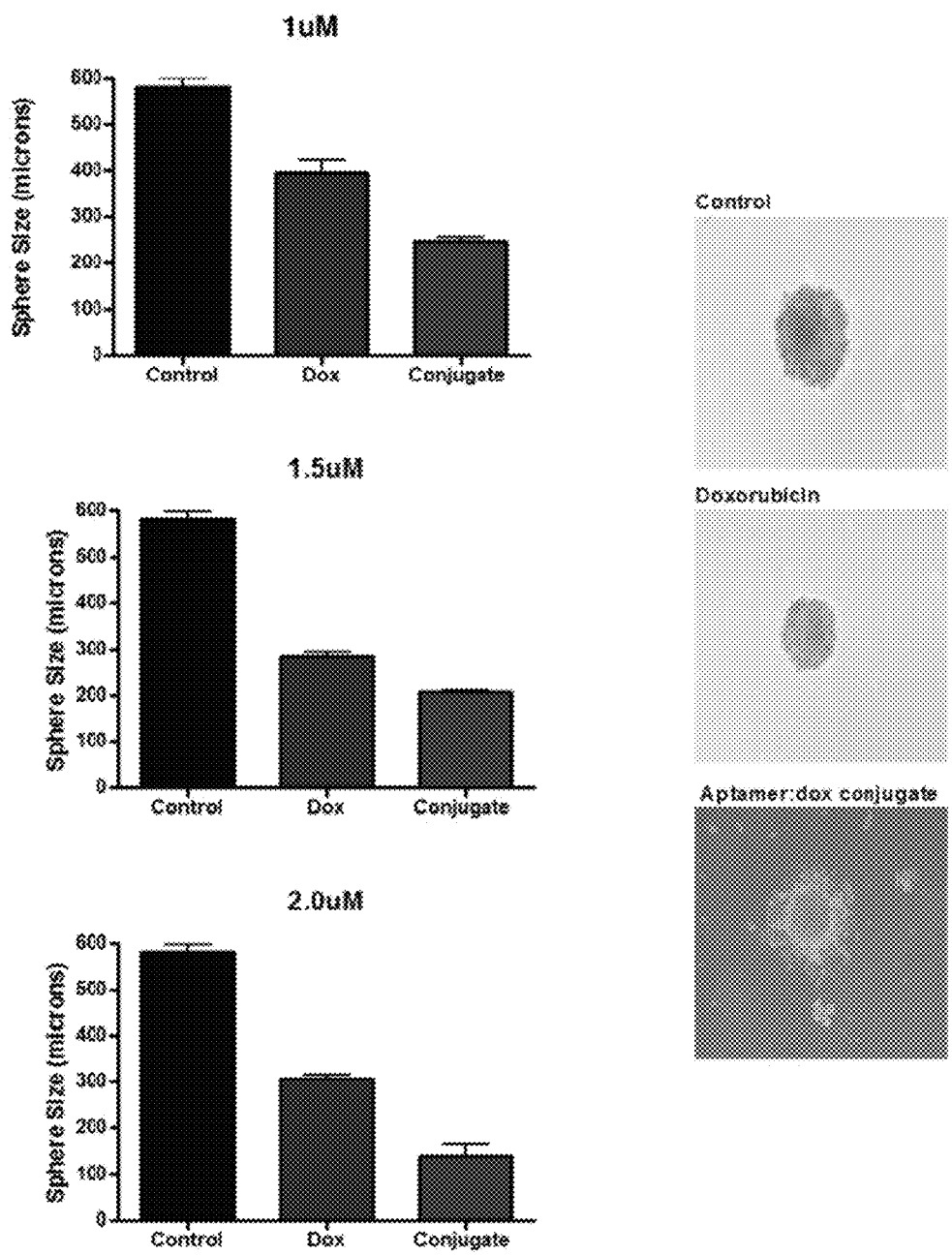

FIG. 10. Tumoursphere size. Measurements were taken of spheres from 500 cells in 96 well plates. Cells were conditioned in sphere control medium, free DOX, and aptamer-Dox conjugate. Decrease in sphere size was seen in all three concentrations between control and conjugate (P<0.01), Data shown are mean±SE, n =3.

Figure 11:
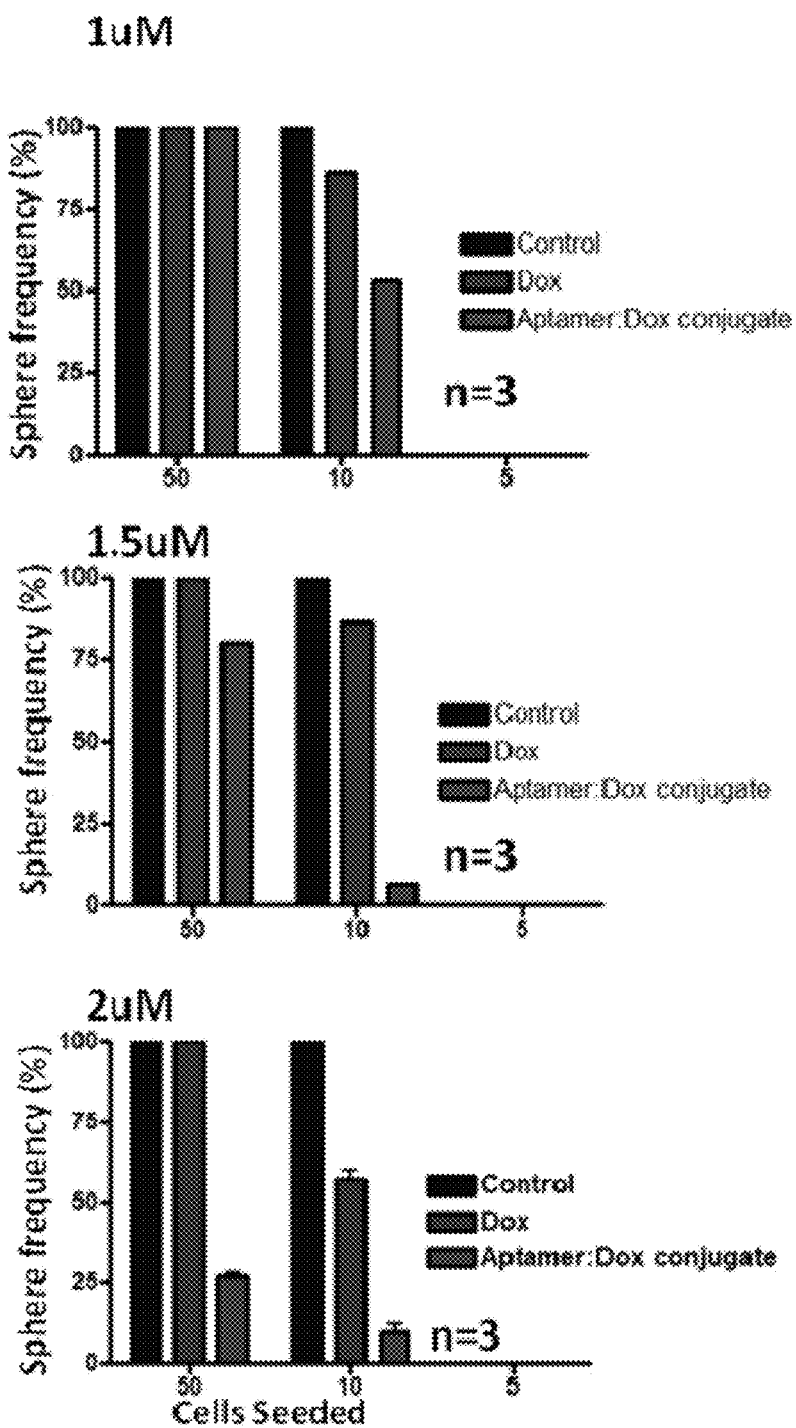

FIG. 11. Sphere formation was measured by the number of spheres formed at different cell concentration within different conditions. 1 μM showed no change at 50 cells but clear difference in control and conjugate formation (P<0.01) at 10 cells. Increasing the concentration of the conventional and novel drug results in a greater inhibition of sphere formation between control and conjugate (P<0.001). This effect was seen at 50 cells when the concentration increase to 2 μM (P<0.001). In all of these the CD133 aptamer-Dox conjugate a significant difference in tumoursphere inhibition compared to free DOX (P<0.01).

Figure 12:
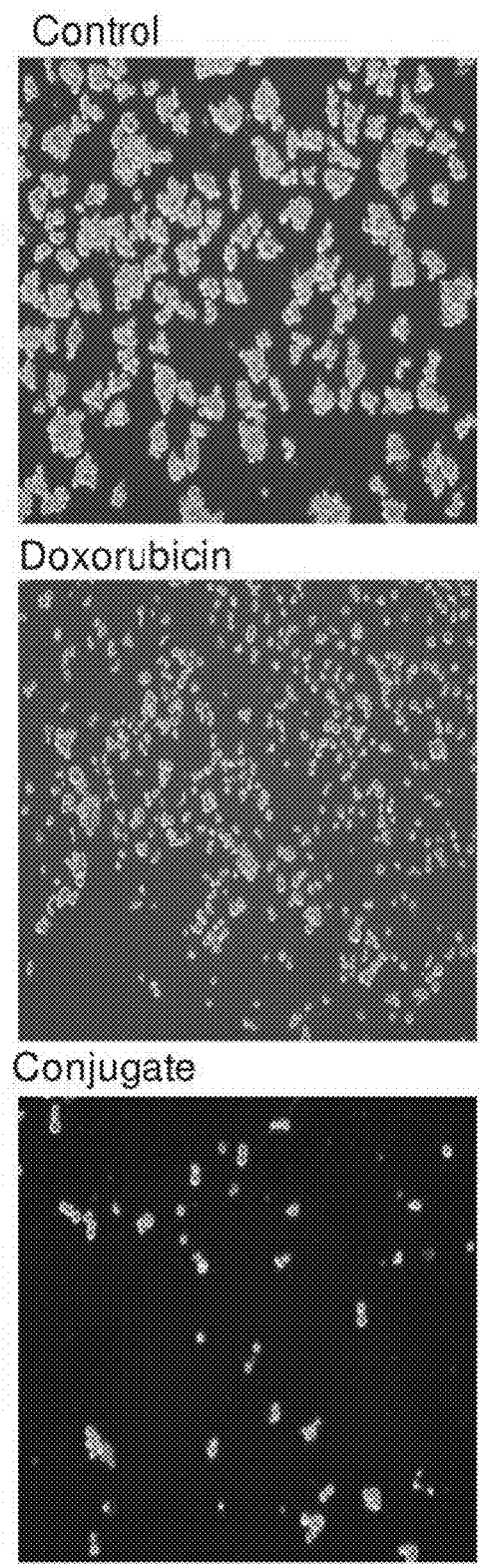

FIG. 12. Visualisation of tumourspheres using a 6 well ultralow attachment plate.

KEY TO SEQUENCE LISTING

SEQ ID NO:1: is the core nucleotide sequence for the loop region of a CD133 aptamer which is flanked 5' and 3' ends by a length of alternating CG paired nucleotides.

SEQ ID NO:2: is the sequence for a CD133 aptamer which can conjugate DOX.

SEQ ID NO:3: is the core nucleotide sequence for the loop region of a CD133 aptamer.

SEQ ID NO:4: is the sequence for a hybrid RNA/DNA CD133 aptamer flanked 5' and 3' by a length of alternating CG nucleotides and contains an 3' inverted dT.

SEQ ID NO:5: is the sequence for a hybrid RNA/DNA CD133 aptamer.

DETAILED DESCRIPTION OF THE INVENTION

General Techniques and Selected Definitions

The term "and/or", e.g., "X and/or Y" shall be understood to mean either "X and Y" or "X or Y" and shall be taken to provide explicit support for both meanings or for either meaning.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each example described herein is to be applied mutatis mutandis to each and every other example of the disclosure unless specifically stated otherwise.

Those skilled in the art will appreciate that the disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure.

The present disclosure is performed without undue experimentation using, unless otherwise indicated, conventional techniques of molecular biology, recombinant DNA technology, cell biology and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, ppl-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series, Sakakibara, D., Teichman, J., Lien, E. Land Fenichel, R. L. (1976). Biochem. Biophys. Res. Commun. 73 336-342; Merrifield, R.B. (1963). J. Am. Chem. Soc. 85, 2149-2154; Barany, G. and Merrifield, R.B. (1979) in The Peptides (Gross, E. and Meienhofer, J. eds.), vol. 2, pp. 1-284, Academic Press, New York. 12. Wünsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) Int. J. Peptide Protein Res. 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

The term "consists of" or "consisting of" shall be understood to mean that a method, process or composition of matter (e.g. aptamer sequence) has the recited steps and/or components and no additional steps or components.

The term "consists essentially of" or "consisting essentially of" in the context of a nucleic acid sequence as used herein is to be construed non-exhaustively and is understood to mean a nucleotide sequence wherein additional nucleotide bases may be present wherein said additional bases constitute no more than about 10% of the total nucleotide sequence.

The term "about", as used herein when referring to a measurable value such as an amount of weight, time, dose, etc. is meant to encompass variations of ±20% or ±10%, more preferably ±5%, even more preferably ±1%, and still more preferably ±0.1% from the specified amount.

The term "aptamer" or "oligonucleotide aptamer" as used herein refers in general to either an oligonucleotide of a single defined sequence or a mixture of said oligonucleotides, wherein the mixture retains the properties of binding specifically to CD133. As used herein, "aptamer" refers to single stranded nucleic acid. Structurally, the aptamers of the present disclosure are specifically binding oligonucleotides. Aptamers may comprise RNA, DNA or both RNA and DNA. The aptamer may be synthetically produced using art known methods. Alternatively the aptamer may be recombinantly produced.

The term "oligonucleotide" as used herein is generic to polydeoxyribonucleotides (containing 2'-deoxy-D-ribose or modified forms thereof), i.e. DNA, to polyribonucleotides (containing D ribose or modified forms thereof), i.e. RNA, and to any other type of polynucleotide which is an N-glycoside or C-glycoside of a purine or pyrimidine base, or modified purine or pyrimidine base or abasic nucleotides. According to the present disclosure the term "oligonucleotide" includes not only those with conventional bases, sugar residues and internucleotide linkages, but also those that contain modifications of any or all of these three moieties.

The term "CG paired nucleotides" as used herein is understood to refer to the base pairing of complementary C and G nucleotides when present in a double stranded configuration. For example, a single CG pared nucleotide would correspond to a C on ne strand base paired with G on the complementary strand. 4 CG paired nucleotides refers to a configuration in which CGCG or GCGC is present in a linear sequence on one strand and is base paired with the complementary sequence GCGC or CGCG on the complementary strand.

The "term CpG site" as used herein is understood to refer to a region of DNA wherein a cytosine nucleotide occurs next to a guanine nucleotide in the linear sequence of bases along its length. The term CpG is short for C-phosphate-G, that is, cytosine and guanine separated by only one phosphate. The CpG notation is used to distinguish the linear sequence from the CG base pairing of cytosine and guanine.

The term "RNA-DNA hybrid aptamer" as used herein is an aptamer comprising ribonucleoside units and deoxyribonucleoside units or bases.

The term "pyrimidine" as used herein refers to cytosine (C), thymidine (T) or uracil (U) bases. Thymine (T) is usually found in DNA but can appear in RNA. Cytosine is found in both RNA and DNA and uracil is usually found in RNA but can appear in DNA.

As used herein the term "binding affinity" is intended to refer to the tendency of an aptamer to bind or not bind a target and describes the measure of the strength of the binding or affinity of the aptamer to bind the target. The energetics of said interactions are significant in "binding affinity" because they define the necessary concentrations of interacting partners, the rates at which these partners are capable of associating, and the relative concentrations of bound and free molecules in a solution. The energetics are characterized herein through, among other ways, by the determination of a dissociation constant, $K_d$. As is known in the art, a low dissociation constant indicates stronger binding and affinity of the molecules to each other.

As used herein, the term "biological sample" refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" will contain cells from the subject. In the present disclosure the "biological sample" will include CD133 expressing cells. Biological samples include, but are not limited to, tissue biopsies, needle biopsies, scrapes (e.g. buccal scrapes), whole blood, plasma, serum, lymph, bone marrow, urine, saliva, sputum, cell culture, pleural fluid, pericardial fluid, ascitic fluid or cerebrospinal fluid. Biological samples also include tissue biopsies and cell cultures. A biological sample or tissue sample can refer to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the sample is from a resection, bronchoscopic biopsy, or core needle biopsy of a primary or metastatic tumor, or a cellblock from pleural fluid. In addition, fine needle aspirate samples can be used. Samples may be paraffin-embedded or frozen tissue. The sample can be obtained by removing a sample of cells from a subject.

The term "sufficient to permit attachment of a least one moiety thereto" is to be given a broad interpretation. The term encompasses direct attachment or connection or non-direct attachment or connection (e.g. covalent bond or electrostatic interaction), or a reversible inclusion or insertion (e.g. intercalation). In another example, the attachment is by conjugation or by use of a linker.

The term "coupled to" as used herein is intended to encompass any construction whereby the aptamer is linked, attached or joined to a 3' or 5' terminal agent as described herein (e.g. invdT) or to a moiety as described herein.

The term "having substantially the same ability" is understood to mean that an aptamer that is capable of competitively inhibiting the binding of the aptamer of the present disclosure to an epitope on CD133. Methods for determining whether an aptamer is capable of competitively inhibiting the binding to CD133 of the apatmer of the present disclosure may involve competitive binding assays known in the art.

The term "isolated" as used herein is intended to refer to the aptamer purified from other components or chemicals which may be present during the process of generating and purifying the aptamer (e.g. using the SELEX method). In the context of cells, the term also refers to cells isolatable or purified from other components in the environment in which it may naturally occur. The isolated cell may be purified to any degree relative to its naturally-obtainable state.

The term "fragment of an immunoglobulin" may be used interchangeably with "antigen binding fragment and is understood to refer to one or more variable regions of an intact antibody. Examples of antibody fragments include Fab, Fab', F(ab')2 and Fv fragments; diabodies; linear antibodies; single-chain antibody molecules and multispecific antibodies formed from antibody fragments.

As used herein, the term "therapeutically effective amount" shall be taken to mean a sufficient quantity of aptamer or pharmaceutical composition according to the present disclosure to reduce the number of CD133 expressing cancer stem cells and/or one or more symptoms of cancer. The skilled artisan will be aware that such an amount will vary depending upon, for example, the particular subject and/or the type or severity or level of disease. The term is not be construed to limit the present disclosure to a specific quantity of aptamer.

As used herein, the term "treat" or "treatment" or "treating" shall be understood to mean administering a therapeutically effective amount of aptamer or pharmaceutical composition as disclosed herein and reducing at least one symptom of a clinical condition associated with or caused by cancer.

As used herein, the term "specifically binds" shall be taken to mean that the aptamer reacts or associates more frequently, more rapidly, with greater duration and/or with greater affinity with a particular cell or substance than it does with alternative cells or substances. For example, an aptamer that specifically binds to a target protein binds that protein or an epitope or immunogenic fragment thereof with greater affinity, avidity, more readily, and/or with greater duration than it binds to unrelated protein and/or epitopes or immunogenic fragments thereof. It is also understood by reading this definition that, for example, a aptamer that specifically binds to a first target may or may not specifically bind to a second target. As such, "specific binding" does not necessarily require exclusive binding or non-detectable binding of another target, this is encompassed by the term "selective binding". Generally, but not necessarily, reference to binding means specific binding. The specificity of binding is defined in terms of the comparative dissociation constants (Kd) of the aptamer for target as compared to the dissociation constant with respect to the aptamer and other materials in the environment or unrelated molecules in general. Typically, the Kd for the aptamer with respect to the target will be 2-fold, 5-fold, or 10-fold less than the Kd with respect to the target and the unrelated material or accompanying material in the environment. Even more preferably, the Kd will be 50-fold, 100-fold or 200-fold less.

The term "selective binding" shall be taken to mean exclusive binding or non-detectable binding of the aptamer to a marker or antigen expressed on a cell, wherein the marker or antigen is other than CD133.

The term "CD133+" or "CD133 expressing cell" as used herein may be used interchangeably. The term encompasses cell surface expression of the CD133 antigen which can be detected by any suitable means. In one example, reference to a cell being positive for a given marker means it may be either a low (lo or dim) or a high (bright, bri) expresser of that marker depending on the degree to which the marker is present on the cell surface, where the terms relate to intensity of fluorescence.

Figure 1:
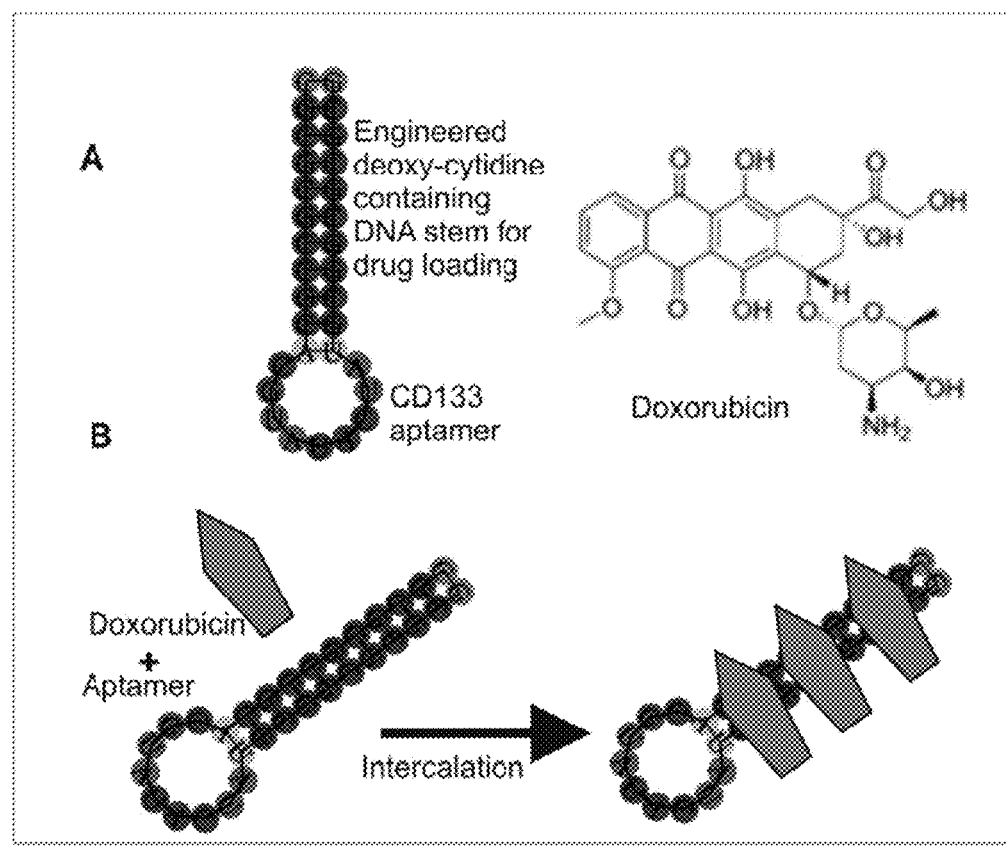
FIG. 1. Schematic diagram of predicted intercalation of DOX to modified CD133 aptamer. (A) The secondary structure of the aptamer determined via VIENNA software (left) and the molecular structure of doxorubicin (right) (B) Representation of possible intercalation between the aptamer and DOX due to the drugs high affinity for double stranded G-C pairing.

As used herein, the term "theranostic" or "theranostic agent" is understood to mean an aptamer which incorporates both diagnostic and therapeutic functionalities. Such entities can be used for simultaneous targeted drug delivery and release, and diagnosis including monitoring disease progression and response to therapy. More particularly, the theranostic agent according to the present disclosure is one in which a chemotherapeutic molecule e.g. doxorubicin is conjugated to the aptamer so as to form an aptamer-Dox conjugate. The term "aptamer-Dox conjugate" is understood as referring to a CD133 apatmer of the present disclosure in which one or more doxorubicin molecules is intercalated in the aptamer stem sequence as shown in FIG. 1.

As used herein, the term "subject" shall be taken to mean any subject, including a human or non-human subject. The non-human subject may include non-human primates, ungulate (bovines, porcines, ovines, caprines, equines, buffalo and bison), canine, feline, lagomorph (rabbits, hares and pikas), rodent (mouse, rat, guinea pig, hamster and gerbil), avian, and fish. In one example, the subject is a human.

Aptamers

Several unique properties of aptamers make them attractive tools for use in a wide array of molecular biology applications, and as potential pharmaceutical agents. First, most aptamers bind to targets with high affinity, demonstrating typical dissociation constants in the pico- to nanomolar range. Binding sites for aptamers include clefts and grooves of target molecules resulting in antagonistic activity very similar to many currently available pharmaceutical agents. Second, aptamers are structurally stable across a wide range of temperature and storage conditions, maintaining the ability to form their unique tertiary structures. Third, aptamers can be chemically synthesised, in contrast to the expensive and work-intensive biological systems needed to produce monoclonal antibodies.

Without wishing to be bound by theory, RNA aptamers are generally preferred by many groups due to the theoretically higher affinity of RNA aptamers for their target proteins as well as the greater plasma stability of modified RNA than unmodified RNA.

Disclosed herein are aptamer molecules that specifically bind to the CD133 antigen which can be used for effective intracellular delivery of agents, such as chemotherapy molecules to treat cancer. Such aptamer molecules of the present disclosure are particularly useful as therapeutic, diagnostic and theranostic agents.

Aptamers are single stranded oligonucleotides or oligonucleotide analogs that bind to a particular target molecule, such as a protein or a small molecule. Thus, aptamers are the oligonucleotide analogy to antibodies. In general, aptamers comprise about 15 to about 100 nucleotides, preferably about 15 to about 40 nucleotides, and more preferably about 20 to about 40 nucleotides, in that oligonucleotides of a length that falls within these ranges can be prepared by conventional techniques.

Aptamer binding is highly dependent on the secondary structure formed by the aptamer oligonucleotide. Both RNA and single stranded DNA (or analog) aptamers are known. See, for example, Burke et al (1996). J. Mol. Biol. 264:650-666; Ellington and Szostak (1990). Nature 346:818-22; Hirao et al (1998). Mol Divers. 4:75-89; Jaeger et al (1998). EMBO Journal 17:4535; Kensch et al (2000). J. Biol. Chem 275:18271-8; Schneider et al (1995). Biochemistry 34:9599-9610; and U.S. Pat. Nos. 5,773,598; 6,028,186; 6,110,900; 6,127,119; and 6,171,795.

Aptamers of the present disclosure include hybrid RNA/DNA aptamers in which the binding (i.e. loop) region of the aptamer is RNA and the stem region is DNA. Without wishing to be bound by theory, it is believed that the DNA stem region provides sites for the intercalation of molecules such as doxorubicin due to the molecule's high affinity for double stranded DNA CG pairing.

Aptamer Generation

Various methods for preparing aptamers according to the present disclosure will be familiar to persons skilled in the art. Systematic Evolution of Ligands by Exponential Enrichment, "SELEXTM" is a method for making a nucleic acid ligand for any desired target, as described, e.g., in U.S. Pat. Nos. 5,475,096 and 5,270,163, and PCT/US91/04078, each of which is specifically incorporated herein by reference.

SELEXTM technology is based on the fact that nucleic acids have sufficient capacity for forming a variety of two- and three-dimensional structures and sufficient chemical versatility available within their monomers to act as ligands (i.e., form specific binding pairs) with virtually any chemical compound, whether large or small in size.

The method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the SELEXTM method includes steps of contacting the mixture with the target under conditions favourable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

Within a nucleic acid mixture containing a large number of possible sequences and structures, there is a wide range of binding affinities for a given target. A nucleic acid mixture comprising, for example a 20 nucleotide randomized segment can have 420 candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favour the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about 1018 different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

Enrichment of aptamer candidates during selection may be monitored using restriction fragment length polymorphism (RFLP) and flow cytometry as described in Shigdar S et al (2013) Cancer Letters 330:84-95.

Binding Affinity of Aptamers

The binding affinity describes the measure of the strength of the binding or affinity of molecules to each other. Binding affinity of the aptamer herein with respect to targets and other molecules is defined in terms of Kd. The dissociation constant can be determined by methods known in the art and can be computed even for complex mixtures by methods such as those, for example, set forth in Caceci, M., et al., Byte (1984) 9:340-362. Examples of measuring dissociation constants are described for example in U.S. Pat. No. 7,602,495 which describes surface Plasmon resonance analysis, and in U.S. Pat. No. 6,562,627, and US 2012/00445849. In another example, the Kd is established using a double-filter nitrocellulose filter binding assay such as that disclosed by Wong and Lohman, (1993). Proc. Natl. Acad. Sci. USA 90, 5428-5432. Methods for determining binding affinity of aptamers is also described in for example, Stoltenburg R et al (2005) Anal Bioanal Chem 383:83-91, Tran D T et al (2010) Molecules 15, 1127-1140, and Cho M et al. (2013) PNAS 110(46):18460-18465.

It has been observed, however, that for some small oligonucleotides, direct determination of Kd is difficult, and can lead to misleadingly high results. Under these circumstances, a competitive binding assay for the target molecule or other candidate substance can be conducted with respect to substances known to bind the target or candidate. The value of the concentration at which 50% inhibition occurs (Ki) is, under ideal conditions, equivalent to Kd. However, in no event will a Ki be less than Kd. Thus, determination of Ki, in the alternative, sets a maximal value for the value of Kd. Under those circumstances where technical difficulties preclude accurate measurement of Kd, measurement of Ki can conveniently be substituted to provide an upper limit for Kd. A Ki value can also be used to confirm that an aptamer of the present disclosure binds CD133.

Improving Aptamer Stability

One potential problem encountered in the use of nucleic acids as therapeutics in that oligonucleotides in their phosphodiester form may be quickly degraded in body fluids by intracellular and extracellular enzymes such as endonucleases and exonucleases before the desired effect is manifest. The present disclosure also includes analogs as described herein and/or additional modifications designed to improve one or more characteristics of the aptamers such as protection from nuclease digestion.

Oligonucleotide aptamer modifications contemplated in the present disclosure include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole.

Modifications to generate oligonucleotide aptamers which are resistant to nucleases can also include one or more substitute internucleotide linkages, altered sugars, altered bases, or combinations thereof. Such modifications include 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, and unusual base-pairing combinations such as the isobases isocytidine and isoguanosine; 3' and 5' modifications such as capping; conjugation to a high molecular weight, non-immunogenic compound; conjugation to a lipophilic compound; and phosphate backbone modification.

In one example, the non-immunogenic, high molecular weight compound conjugated to the aptamer of the present disclosure is polyalkylene glycol, preferably polyethylene glycol. In one example, the backbone modification comprises incorporation of one or more phosphorothioates into the phosphate backbone. In another example, the aptamer of the present disclosure comprises the incorporation of fewer than 10, fewer than 6, or fewer than 3 phosphorothioates in the phosphate backbone.

Where appropriate, additional modification may include at least one of the following, 2'-deoxy, 2'-halo (including 2'-fluoro), 2'-amino (preferably not substituted or mono- or disubstituted), 2'-mono-, di- or tri-halomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or C15 alkyl groups, abasic linkers, 3'-deoxy-adenosine as well as other available "chain terminator" or "non-extendible" analogs (at the 3'-end of the RNA), or labels such as 32P, 33P and the like. All of the foregoing can be incorporated into an aptamer using the standard synthesis techniques disclosed herein.

Utility of the Aptamers

The aptamer molecules of the present disclosure can be used as affinity ligands to separate and purify target molecules (e.g. CD133 bearing cancer stem cells), as probes to trace, monitor, detect and quantitate target molecules (e.g. CD133 bearing cancer stem cells), or to block, allow, activate or catalyse reactions that are physiologically relevant to achieve therapeutic effect. They can act as pharmaceutical agent, bind to a specific target and direct specific molecules to a desired site.

The aptamer molecules of the present disclosure can be used in in vitro processes, for example affinity purification mixtures to purify target molecules (e.g. CD133 bearing cancer stem cells). The aptamers are ideal for chromatographic separations of target molecules (e.g. CD133 bearing cancer stem cells) from contaminants and for purifying target molecules from cell cultures or cell extracts.

In one example, the aptamer molecules of the present disclosure can be used as a capture agent to bind or immobilise a target (e.g. CD133 bearing cancer stem cells) to a solid support. The solid support can be comprised of substrates having the structure and composition commonly associated with filters, wafers, wafer chips, membranes and thin films. However, it is contemplated that the solid support may be comprised of substrates including, but not limited to resins, affinity resins, magnetic or polymer beads, or any diagnostic detection reagent, to capture or immobilise reagents for diagnostic, detection or quantitative studies, The solid supports may comprise any material depending of the desired use, including but not limited to glass, metal surfaces and materials such as steel, ceramic or polymeric materials such as polyethylene, polypropylene, polyamide, and polyvinylidenefluoride etc or combinations thereof.

CD133 Antigen

CD133, originally known as AC133 is a glycoprotein (also known as Prominin 1). It is a member of pentaspan transmembrane glycoproteins which specifically localise to cellular protrusions. CD133 is expressed in hematopoietic stem cells, endothelial progenitor cells, gliobalstoma, neuronal and glial stem cells, carious pediatric brain tumors, as well as adult kidney, mammary glands, trachea, salivary glands, placenta, digestive tract, testes and other cell types.

Binding to CD133 Expressing Cancer Stem Cells

The best known example of adult cell renewal by the differentiation of stem cells is the hematopoietic system. Developmentally immature precursors such as hematopoietic stem cells and progenitor cells respond to molecular signals to gradually form the varied blood and lymphoid cell types. Stem cells are also found in other tissues, including epithelial tissues and mesenchymal tissues. Cancer stem cells may arise from any of these cell types, for example, as a result of genetic damage in normal stem cells or by the dysregulated proliferation of stem cells and/or differentiated cells.

Cancer stem cells may be derived from any cancer comprising tumorigenic stem cells, i.e. cells having an ability to proliferate extensively or indefinitely, and which give rise to the majority of cancer cells. Within an established tumour, most cells have lost the ability to proliferate extensively and form new tumours, and a small subset of cancer stem cells proliferate to thereby regenerate the cancer stem cells as well as give rise to tumour cells lacking tumourigenic potential. Cancer stem cells may divide asymmetrically and symmetrically and may show variable rates of proliferation. Cancer stem cell may include transit amplifying cells or progenitor cells that have reacquired stem cell properties.

Representative cancers from which stem cells may be isolated include cancers characterised by solid tumors, including for example fibrosarcoma, myxosarcoma, liposarcoma, chondrosarcoma, osteogenic sarcoma, chordoma, angiosarcoma, endotheliosarcoma, lymphangiosarcoma, synovioma, lymphagioendotheliosarcoma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma.

Additional representative cancers from which stem cells can be isolated or enriched according to the present disclosure include hematopoietic malignancies, such as B cell lymphomas and leukemias, including low grade/follicular non-Hodgkin's lymphoma (NHL), small lymphocytic (SL) NHL, intermediate grade/follicular NHL, intermediate grade diffuse NHL, high grade immunoblastic NHL, high grade small non-cleaved cell NHL, bulky disease NHL and Waldenstrom's Macroglobulinemia, chronic leukocytic leukemia, acute myelogenous leukemia, chronic myelogenous leukemia, lymphoblastic leukemia, lymphocytic leukemia, monocytic leukemia, myelogenous leukemia and promyelocytic leukemia.

Cancer stem cells bearing CD133 may be selected using the aptamer molecules as described herein. For example, aptamers which are coupled to fluorescent dyes can be used for the positive selection of cancer stem cells. CD133 is also known to be expressed in some normal cells. However, CD133 expression is thought to be upregulated in cancer stem cells. Cancer stem cell markers are typically expressed at a level that is at least about 5-fold greater than differentiated cells of the same origin or non-tumorigenic cells, for example, at least about 10-fold greater, or at least about 15-fold greater, or at least about 20-fold greater, or at least about 50-fold greater, or at least about 100-fold greater. The selection process may also include negative selection markers which can be used for the elimination of those cancer cells in the population that are not cancer stem cells.

It will be understood that in performing the present disclosure, separation of cells bearing CD133 can be effected by a number of different methods. For example, the aptamer of the present disclosure may be attached to a solid support to allow for a crude separation. Various techniques of different efficacy may be employed depending upon efficiency of separation, associated cytotoxicity, ease and speed of performance and necessity for sophisticated equipment and/or technical skill. Procedures for isolation or purification may include, but are not limited to, magnetic separation using aptamer-coated magnetic beads, affinity chromatography and "panning" with aptamer attached to a solid matrix. Techniques providing accurate isolation or purification include but are not limited to FACS. Methods for preparing FACS will be apparent to the skilled artisan.

Enrichment of CD133 Expressing Cancer Stem Cells

The aptamers of the present disclosure may be used to enrich cancer stem cells from a biological sample obtained from a subject. Typically the subject will be one which has a tumour or is suspected of having a tumor containing cancer stem cells. The term "enriched" or "enrichment" or variations thereof are used herein to describe a population of cells in which the proportion of one particular cell type (i.e. cancer stem cells) is increased when compared with an untreated population of the cells (e.g. cells in the sample).

In one example, a population enriched for cancer stem cells comprises at least about 0.1%, or 0.5% or 1% or 2% or 5% or 10% or 15% or 20% or 25% or 30% or 50% or 75% 80%, or 85%, or 90%, or 95% CD133 bearing (positive) cancer stem cells. In this regard, the term "enriched cell population comprising cancer stem cells" will be taken to provide explicit support for the term "population of cells comprising X % cancer stem cells, wherein X % is a percentage as recited herein.

In one example, the population of cells is enriched from a cell preparation comprising CD133+ cells in a selectable form. In this regard, the term "selectable form" will be understood to mean that the cells express a marker (e.g. a cell surface marker) permitting selection of CD133 bearing cells.

Diagnosis/Detection of Cancer Using Aptamer Molecules

The aptamers of the present disclosure can be used in vitro for diagnostic and/or detection purposes to determine the presence of cancer stem cells in malignant tissue. The method involves examining a biological sample for the presence of CD133+ cancer stem cells. For example, the biological sample can be contacted with a labelled aptamer of the present disclosure or an Aptamer-Dox of the present disclosure and the ability of the aptamer to specifically bind to the cells in the sample is determined. Binding indicates the presence of a CD133 bearing cancer stem cell. The aptamer of the present disclosure can also be used to localise a tumor in vivo by administering to a subject an aptamer of the present disclosure which is labelled with a reporter group which gives a detectable signal. Alternatively, or additionally, because doxorubicin has inherent fluorescent activity (particularly at the far infra-red wavelength) this feature can be exploited for diagnosis. Bound aptamers can then be detected using flow cytometry, microscopy, external scintigraphy, emission tomography, optical imaging or radionuclear scanning. The method can be used to stage a cancer in a subject with respect to the extent of the disease and to monitor changes in response to therapy.

Detection of cancer stem cells can be facilitated by coupling the aptamer to a detectable label. Examples of detectable labels include various enzymes, prosthetic groups, fluorescent materials, luminescent materials, bioluminescent materials, electron dense labels, labels for MRI, and radioactive materials. Examples of suitable enzymes include horseradish peroxidise, alkaline phosphatise, β-galactosidase, or acetylcholinesterase. Examples of suitable prosthetic group complexes include streptavidin/biotin and avidin/biotin. Examples of suitable fluorescent materials include umbellifone, fluorescein isothiocyanate, rhodamine, dischlorotriazinylamine fluorescein, dansyl chloride or phycoerythrin. An example of a luminescent material includes luminol. Examples of bioluminescent materials include luciferase, luciferin, and aequorin, and examples of suitable radioactive material include 125I, 131I, 35S, 18F, 64Cu, 94mTc, 124I, 11C, 13N, 15O, 68Ga, 86Y, 82Rb or 3H.

Labelling at the 3' end of the aptamer can be achieved, for example by templated extension using Klenow polymerase, by T4 ligase-mediated ligation and by terminal deoxynucleotidyl transferase. Labelling at the 5' end can be achieved by the supplementation of the in vitro transcription mix with an excess of GTP-β-S, the thiol of which can then be used to attach biotin. In addition, direct chemical conjugation of a suitable group(s) to either 5'- or 3'-end can be used to label the aptamers.

Use of the Aptamers in Cancer Treatment and Theranostics

The aptamers of the present disclosure can be coupled to a moiety and used to direct the moiety to CD133+ cells, preferably cancer stem cells. Examples of moieties include toxins, radionuclides, or chemotherapeutic agents which can be used to kill cancer stem cells.

The aptamer can be fused to the moiety, e.g. the toxin, either by virtue of the moiety and aptamer being chemically synthesised, or by means of conjugation, e.g. a non-peptide covalent bond, e.g. a non-amide bond, which is used to join separately produced aptamer and the moiety. Alternatively, the aptamer and moiety may be joined by virtue of a suitable linker peptide.

Useful toxin molecules include peptide toxins, which are significantly cytotoxic when present intracellularly. Examples of toxins include cytotoxins, metabolic disrupters (inhibitors and activators) that disrupt enzymatic activity and thereby kill cancer stem cells, and radioactive molecules that kill all cells within a defined radius of the effector portion. A metabolic disrupter is a molecule, e.g. an enzyme or a cytokine that changes the metabolism of a cell such that is normal function is altered. Broadly, the term toxin includes any effector that causes death to a tumour cell.

Many peptide toxins have a generalised eukaryotic receptor binding domain; in these instances the toxin must be modified to prevent killing cells not bearing CD133 (e.g. to prevent killing cells not bearing CD133 but having a receptor for the unmodified toxin). Such modifications must be made in a manner that preserves the cytotoxic function of the molecule. Potentially useful toxins include, but are not limited to diphtheria toxin, cholera toxin, ricin, 0-Shiga-like toxin (SLT-I, SLT-II, SLT-IIV), LT toxin, C3 toxin, Shiga toxin pertussis toxin, tetanus toxin, Pseudomonas exotoxin, alorin, saponin, modeccin and gelanin. Other toxins include tumor necrosis actor alpha (TNF-alpha) and lymphotoxin (LT). Another toxin which has antitumor activity is calicheamicin gamma 1, a diyne-ene containing antitumor antibiotic with considerable potency against tumors (Zein Net al (1988). Science 240:1198-201).

As an example, diphtheria toxin (which sequence is known) can be conjugated to the aptamers of the present disclosure. The natural diphtheria toxin molecule secreted by Corynebacterium diptheriae consist of several functional domains that can be characterised, starting at the amino terminal end of the molecule, as enzymatically-active fragment A (AA 1-193) and fragment B (AA 194-535) which includes a translocation domain and a generalised cell binding domain (AA 475-535).

The aptamer and the toxin moiety can be linked in any of several ways which will be known to persons skilled in the art. For example, a method of conjugating an aptamer to a toxin (gelonin) is described in Chu T C et al. (2006) Cancer Res 6(12)5989-5992.

The moiety can also be a modulator of the immune system that either activates or inhibits the body's immune system at the local level. For example, cytokines e.g. lymphokines such as IL-2, delivered to a tumour can cause the proliferation of cytotoxic T-lymphocytes or natural killer cells in the vicinity of the tumour.

The moiety or reporter group can also be a radioactive molecule, e.g. a radionucleotide, or a so-called sensitizer, e.g. a precursor molecule that becomes radioactive under specific conditions, e.g. boron when exposed to a bean of low-energy neutrons, in the so-called "boron neutron capture therapy" (BNCT) as described in Barth et al. (1990). Scientific American Oct 1990:100-107. Compounds with such radioactive effector portions can be used both to inhibit proliferation of cancer stem cells in the tumor and to label the cancer stem cells for imaging purposes.

Radionucleotides are single atom radioactive molecules that can emit either $\alpha$, $\beta$, or $\gamma$ particles. Alpha particle emitters are preferred to $\beta$, or $\gamma$ particle emitters, because they release far higher energy emissions over a shorter distance, and are therefore efficient without significantly penetrating, and harming, normal tissues. Suitable a particle emitting radionuclides include 211At, 212Pb, and 212Bi.

The radioactive molecule may be tightly linked to the aptamer either directly or by a bifunctional chelate. This chelate must not allow elution and thus premature release of the radioactive molecule in vivo. Waldmann, Science, 252: 1657-62 (1991). As an example, to adapt BNCT to the present invention, a stable isotope of boron, e.g., boron 10, can be selected as the antitumor moiety or effector portion of the compound. The boron will be delivered to and concentrates in or on the tumor cells by the specific binding of the aptamer to the cancer stem cell. After a time that allows a sufficient amount of the boron to accumulate, the tumor can be imaged and irradiated with a beam of low-energy neutrons, having an energy of about 0.025 eV. While this neutron irradiation, by itself, causes little damage to either the healthy tissue surrounding the tumor, or the tumor itself, boron 10 (e.g., on the surface of a tumor cell) will capture the neutrons, thereby forming an unstable isotope, boron 11. Boron 11 instantly fissions yielding lithium 7 nuclei and energetic a particles, about 2.79 million Ev. These heavy particles are a highly lethal, but very localized, form of radiation, because particles have a path length of only about one cell diameter (10 microns).

Suitable chemotherapeutic agents that may be attached to the apatmer of the present disclosure may be selected from doxorubicin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1 de-hydrotestosterone, glucocorticoids, procaine, tetracaine, lidocaine, propranolol, and puromycin, antimetabolites (such as methotrexate, 6-mercaptopurine, 6 thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), idarubicin, mithramycin, mitomycin, mitoxantrone, plicamycin, anthramycin (AMC)).

Alternatively, the moiety is a chemotherapeutic molecule or other molecule which is capable of intercalating into the stem region sequence of the aptamer. For example, where the chemotherapeutic molecule is doxorubicin, the molecule is capable of intercalating at CpG sites in the DNA of the aptamer stem. Chemotherapeutic agents such as doxorubicin are intrinsically fluorescent which makes them convenient for probing and visualising their location with various imaging technologies. The therapeutic and imaging capabilities combined in a DOX molecule make it suitable for use as a theranostic agent. Accordingly, the aptamers of the present disclosure can be used as theranostic agents to deliver doxorubin to cancer stem cells. In order to increase aqueous solubility, the amino group of the sugar in doxorubicin can be protonated by forming a DOX hydrochloride.

Moieties that are capable of intercalating into the aptamers of the present disclosure include, doxorubicin, adriamycine, berberine, provflavine, mitoxantrone, daunorubicin, thalidomide, dactinomycin, danomycin, actinomycin D, 9-aminoacridine, amrubicin, amsacrine, anthramycine, berbine, bleomycin, elliplicine, epirubicin, idarubicin, methpyrillo, mithramycin, mitomycin, mitomycin C, mitoxantrone, mitoxantrone, pirarubicin, pixantrone, plicamycin, proflavine, prodigiosin, thalidomide, voreloxin, valrubicin, zorubicin. chlorpheniramine, prodisiosin, methapyrillino, mitomycin, distamycin, dantinomycin, distamycin, carboplatin, cisplatin and other platinum derivatives, Hoechst 33258, berenil, DAPI or carcinogenic agents (including the exo 8,9 epoxide of aflatoxin B1, acridines such as proflavine or quinacrine or ethidium bromide). Other GC intercalating agents will be familiar to persons skilled in the art of the present invention and are intended to be included within the scope of the present disclosure.

The aptamer of the present disclosure can also be used for siRNA, ribozyme, or DNAzyme delivery into cells.

Examples of suitable siRNA, ribozyme or therapeutic agent will depend upon the circumstances. Examples of siRNAs or ribozymes that are suitable for use according to the present disclosure include those which target ATP binding cassette membrane transporters, stemness genes (Bmi-1, Notch 1, Sox 2, Oct-4, Nanog, β-catenin, Smo, nestin, ABCG2, Wnt2 and SCF, etc), GAPDH (glyceraldehyde 3-phosphate dehydrogenase), and survivin.

By way of example, this has been demonstrated in the prior art using an anti-PSMA aptamer. Based on the knowledge that PSMA is internalised via clathrin-coated pits to endosome, it was postulated that the anti-PSMA aptamer would carry the attached siRNA to the cells that express PSMA, and the aptamer-siRNA bound to the PSMA protein would gain access to the cell via internalisation. Next, the siRNA portion would undergo processing by the Dicer complex and feed into the RNA-Induced Silencing Complex (RISC)-mediated gene-silencing pathway. Three groups have utilised different strategies to accomplish this. Chu et al (2006) Nucleic Acids Res 34, e73 describes a biotin-streptavidin bridge mediated conjugation method to assemble the anti-PSMA aptamer and the siRNA. McNamara et al. (2006) Nat Biotechnol 24, 1005-1015 used a "RNA-only" aptamer-siRNA chimera approach to link the aptamer and the siRNA. In a subsequent study by Wullner et al (2008). Curr. Cancer Drug Targets 8:554-565, the authors used the anti-PSMA aptamer to deliver Eukaryotic Elongation Factor 2 (EEF2) siRNA to PSMA-positive prostate cancer cells, Bivalent PSMA aptamers were used for this purpose. The authors demonstrated that, compared to the monovlaent anti-PSMA-siRNA chimera, the gene knockdown potency of the bivalent aptamer-construct was superior.

The aptamers of the present disclosure can also be used to deliver cargo into CD133+ cancer stem cells in a variety of solid tumours. Gelonin is a ribosomal toxin that can inhibit the process of protein synthesis and is cytotoxic. However, it is membrane impermeable and needs an usher for its cellular entry. Thus, the aptamers of the present disclosure can be utilised to deliver membrane impermeable toxic payload to cancer stem cells. In another embodiment the aptamers of the present invention can be used to deliver Doxorubicin (DOX), a DNA intercalating chemotherapeutic agent that is unable to target cancer stem cells on its own, to $CD133^+$ cancer stem cells.

Tumor resistance to cytotoxic chemotherapeutic agents is due in part to insufficient delivery to and uptake, and more importantly, efflux by cancer cells. Biodegradable nanoparticle (NP) derived from poly(D,L-lactic-co-glycolic acid) PLGA were used to address this problem as described in Dhar et al (2008) Proc. Natl. Acad. Sci. USA 105:17356-17361. Briefly, cisplatin was converted to its pro-drug, Pt(IV) compound, by introducing two alkyl chains. This increased the hydrophobicity of the compound and eased the process of its packaging within the hydrophobic core of the NP. Polyethylene glycol (PEG) was used as a copolymer during the nanoprecipitation step to synthesise the PLGA-PEG nanoparticle. The PLGA-PEG-NP surface was decorated with a PSMA (prostate specific membrane antigen) aptamer. The NP underwent endocytosis when incubated with LNCaP cells, and the alkylated pro-drug was converted to cisplatin by the cytosolic reduction process.

The present disclosure also extends to the use of the aptamer molecules as simultaneous drug delivery and imaging agents (theranostics). This can be achieved by conjugating the aptamer to the surface of a fluorescent quantum dot (QD). Next, the QD-aptamer conjugate is incubated with Dox to form the QD-aptamer-Dox nanoparticle. Both Dox and QD are fluorescent molecules. However, due to their proximity in the QD-aptamer-Dox nanoparticle, they quench each other's fluorescence by a bi-fluorescence resonance energy transfer (FRET) mechanism. Thus, the QD-aptamer-Dox nanoparticle is non-fluorescent. However, internalisation of the QD-aptamer-Dox nanoparticle via PSMA-mediated endocytosis in prostate cancer cells causes the release of Dox from the QD-aptamer-Dox nanoparticles, that results in the recovery of fluorescence by both Dox and QD.

Pharmaceutical Compositions

The present disclosure further provides a pharmaceutical composition comprising the aptamer, diagnostic agent or theranostic agent as described herein. A pharmaceutical composition of the present disclosure includes composition prepared for storage or administration that include a pharmaceutically effective amount of the aptamer in a pharmaceutically acceptable carrier and/or excipient. The choice of excipient or other elements of the composition can be adapted in accordance with the route and device used for administration.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g. water, saline, aqueous dextrose, lactose, Ringer's solution a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

Other general additives such as anti-oxidative agent, buffer solution, bacteriostatic agent etc can be added. In order to prepare injectable solutions, pills, capsules, granules, or tablets, diluents, dispersing agents, surfactants, binders and lubricants can be additionally added.

The aptamers of the disclosure and formulations thereof may be administered directly or topically (e.g., locally) to the patient or target tissue or organ as is generally known in the art. For example, a composition can comprise a delivery vehicle, including liposomes, for administration to a subject. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors.

Delivery systems which may be used with the aptamers of the present disclosure include, for example, aqueous and non-aqueous gels, creams, multiple emulsions, microemulsions, liposomes, ointments, aqueous and non-aqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

A pharmaceutical composition of the disclosure is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition from exerting its effect.

The aptamer or composition comprising the aptamer of the present disclosure can be administered parenterally (for example, intravenous, hypodermic, local or peritoneal injection). The effective dosage of the aptamer can be determined according to weight, age, gender, health condition, diet, administration frequency, administration method, excretion and severity of a disease. In one example, the aptamer or theranostic agent as described herein contains the aptamer by 10-95 weight %. In another example, the aptamer or theranostic agent contains the aptamer by 25-75 weight %.

Generally, an amount between 0.1 mg/kg and 100 mg/kg body weight/day of active ingredients is administered.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the aptamer in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the aptamer in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the aptamer in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

A sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution, isotonic sodium chloride solution, and an isotonic salt solution containing sodium and potassium chloride. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy. The administration frequency may be one to several times a day, weekly, or monthly.

Combinations of Aptamers

The aptamer molecule(s) of the present disclosure can be used alone or in combination with one or more additional aptamers according to any method disclosed herein. In one example, the aptamer molecule(s) of the present disclosure can be combined with an aptamer that facilitates the detection, purification or enrichment of cancer stem cells. In one example, the additional aptamer comprises the sequence EpDT3 5'-GCGACUGGUUACCCGGUCG-3' as described in Shigdar S et al (2011). Cancer Sci 102(5):991-998. In another example, the additional aptamer binds to a different target, e.g. EpCAM.

The present disclosure also encompasses aptamers which may be lined at their 5' and/or 3' terminus to another aptamer via a linker. Suitable linkers are known in the art and may include polymers such as PEG.

Kits

The present disclosure also provides diagnostic kits for carrying out the methods disclosed herein. In one example, the diagnostic kit includes the aptamer or the diagnostic agent as described herein for detecting CD133 expressing cells (e.g. cancer stem cells).

The kit may also include ancillary agents such as buffering agents and stabilising agents. The diagnostic kit may further include agents for reducing background interference, control reagents and an apparatus for conducting a test. Instructions on how to use the diagnostic kit are generally also included.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

EXAMPLES

Methods

Cell Lines and Cell Culture

HT-29 (human colorectal cancer cells) and HEK293T (human embryonic kidney cells) purchased from the American Type Culture Collection (ATCC, Manassas, Va., USA) were maintained in Dulbecco's Modified Eagle's Medium (DMEM, Invitrogen, Victoria, Australia) and supplemented with 10% foetal calf serum (FCS, Hyclone, USA). Cells were incubated in a water-saturated atmosphere with 5% CO2 at 37° C.

Generation of CD133 Aptamer

Generation of the starting CD133 aptamer was as described in Shigdar S et al (2013) Cancer Letters 330:84-95. The stem region sequence of the aptamer was replaced with a DNA stem as shown in FIG. 1.

Development of Aptamer-Dox Conjugate

The 2D structure of CD133-aptamer was predicted using the VIENNA software (http://rna.tbi.univie.ac.at/). This structure guided a more accurate and efficient preparation for characterisation of Aptamer-Drug conjugate. CD133-Aptamer designed for conjugation with chemotherapy agent Doxorubicin (DOX) (SIGMA-ALDRICH) was synthesized from IBA (Germany) and stored at −80° C. Prior to conjugation, the aptamer was folded by heating at 85° C. for 5 min, slowly cooling to room temperature over 10min, followed by incubation at 37° C. for 15 min. DOX was then mixed well with aptamer in conjugation buffer containing 50 mM NaCl, and 2.5 mM MgCl2 and incubated at 37° C. in Orbital mixer/incubator (RATEK) for 2 hour at 75 r.p.m. The conjugate was then passed through a Sephadex®G-50 column (SIGMA-ALDRICH) to separate the aptamer-Dox conjugate from free DOX. The aptamer-DOX conjugate thus contains one or more DOX molecules which are intercalated into the DNA sequence of the stem region of the aptamer.

Determination of Molar Ratio of DOX and Aptamer

The natural fluorescence of DOX and its subsequent quenching after intercalating with the CD133 aptamer was utilised for the measurement of the extent of DOX conjugation and stability via ultra-violet Spectrocopy (UV-Spec). The conjugation process was studied using different aptamer-Dox molar ratios (0, 0.01, 0.04, 0.08, 0.1, 0.2, 0.3, 0.4, 0.5, and 0.6) and analysed using UV-Spec or a fluorescence plate reader based on a standard curve of free DOX.

Evaluation of DOX Loading Efficiency via HPLC

The DOX loading efficiency at different aptamer/DOX molar ratio was determined by extracting the DOX in the conjugate with acetonitrile, followed by the quantification of DOX using HPLC. Briefly, thirty microlitres of aptamer-Dox conjugate eluted from a Sephadex G-50 column was diluted with 90 µl of acetonitrile and vortexed for 1 min. This solution was then centrifuged for 5 min at 21000×g, and 50 µl of the supernatant was diluted in 150 µL PBS and mixed well prior to another centrifugation for 5 min at 21000×g. One hundred micro-litres of supernatant was withdrawn and subjected to reverse-phase chromatography for determination of DOX concentrations via a C-18 column using HPLC. The DOX was quantified using an on-line UV detector in HPLC. A calibration standard curve was prepared with the standard DOX solution under the same conditions. The drug loading efficiency (DLE) was calculated by the formula: DLE (%)=(DOX loaded in conjugate)/(DOX added)×100%.

Analysis of Aptamer Drug Release

The in vitro release of DOX from aptamer-DOX conjugate was determined using a dialysis method with a Slide-A-Lyzer Dialysis Cassette (molecular weight cut off 3.5 kDa, Thermo SCIENTIFIC, Cat No: 66333). Aptamer-Dox conjugates (400 µL, 1 µg/ml DOX) were added into the cassette. The dialysis cassette was dialyzed against PBS and PBS with 10% FCS at pH 8, 7.4 or 5.0 at 37° C., with gentle agitation in the dark. At various time points (10 min, 0.5 h, 1 h, 4 h, 8 h, 24 h and 48 h), thirty microlitre aliquots of the medium were withdrawn from external buffer for release kinetics analysis, and replaced with 30 µL of fresh medium. The DOX concentration was determined using a fluorescence plate reader (Perkin Elmer Life and Analytical Sciences) by converting the fluorescence intensity to mass of DOX according to a standard curve of DOX concentration vs. its fluorescence intensity. Accumulative release of DOX from aptamer-Dox was expressed as a percentage of the released DOX and plotted as a function of time.

Determination of the Equilibrium Dissociation Between the Aptamer-Dox Conjugate and its Target Cells To minimize the non-specific binding, 1×105 HT29 or HEK293T cells were first incubated with blocking buffer (PBS with 10% FCS, 1% BSA and 1% tRNA) for 20 min. Cells were then washed twice with washing buffer (PBS containing 5% FBS and 2.5 mM MgCl2) and incubated on ice for 1 h with either CD133 aptamer, negative-control aptamer, CD133 aptamer-Dox conjugate or negative-control aptamer-Dox conjugate, all labelled with Cy5 in conjugation buffer (50 mM NaCl, and 2.5 mM MgCl2).

Prior to flow cytometric analysis, cells were again washed twice with washing buffer and then suspended in 150 µl washing buffer. Data was then collected using the flow cytometer (FACS CANTOII, Becton Dickerson) to measure the fluorescence intensity of the aptamer and the binding affinity was determined by normalising the fluorescence intensity with the fluorescent background from that of the negative-control aptamer and then derived using Graph Pad Prism software.

Internalisation of Aptamer-Dox Conjugate

Both HT29 and HEK293T were seeded at $8 \times 10^5$ cells per well in 8-chamber slide for 24 h in preparation for confocal microscopy. Cells were incubated with blocking buffer (PBS with 10% FCS, 1 mg/mL BSA, 0.1 mg/mL tRNA) for 20 min, followed by washing twice with washing buffer (PBS containing 5% FBS, 2.5 mM MgCl2, and 5 mM NaCl) prior to incubation with 200 nM aptamer, negative-control aptamer, aptamer-Dox conjugate or negative-control aptamer-Dox conjugate in conjugation buffer for 30 min at 37° C. Bisbenzimide Hoechst 33342 (3 mg/ml) (Sigma)) was added to the cells during the final 15 min of incubation. The aptamer solution was removed and the cells were washed three times for 5 min each in PBS prior to visualisation using a FluoView FV10i laser scanning confocal microscope (Olympus).

CSC Frequency Analysis In Vitro

Cells were harvested at 80% confluence with trypsin digestion and resuspended as single cells in DMEM/F12 serum-free media following centrifugation (1000×g for 5 min). Cells were plated into 96-well ultralow attachment plates at a density of 5, 10, 50, 100, 500, and 1000 cells per well, or at 4000 cells /well in 6-well ultralow attachment plates for tumoursphere formation. Three experiment groups were used: tumoursphere medium control, free DOX treatment (1, 1.5 and 2 µM) and aptamer-Dox treatment (1, 1.5 and 2 µM equivalent to the same concentration of free DOX). After incubation for 24 h at 37° C. supernatant was removed and replaced with equal volume of fresh CSC medium. A tumoursphere was defined as a cell aggregate with a diameter of over 50 µm with well defined borders. Tumoursphere formation frequency and size were recorded 3 days after seeding. The frequency of CSCs was calculated using the ELDA website (http://bioinf.wehi.edu.au/software/elda/index.html. The tumoursphere formation frequency in 6-well incubation was calculated according to the formula F=Numbers of forming tumourspheres/Number of single cells plated (F is the tumoursphere formation frequency).

Data Analysis

Data and results were reported as mean and standard deviation (mean±S.D.) unless otherwise stated. The differences in the mean values among different groups were analysed using a one-way analysis of variance (ANOVA) using SPSS 13.0 program. P values less than 0.05 were considered to be statistically significant.

Example 1

Conjugation of DOX with CD133 Aptamer

A major issue for current cancer therapeutics is the inability to targeting cancer stem cells (CSCs). In order to develop novel CSC-targeting agents, DOX, a commonly used chemotherapeutic drug that is unable to target CSCs on its own, was conjugated to an aptamer against CD133 cell surface marker. The ability of the conjugated aptamer to maintain functionality was tested by assessing the aptamer's binding affinity and specificity as well as the cytotoxicity of the drug.

The secondary structure of the CD133 aptamer was predicted using the VIENNA software (http://rna.tbi.univie.ac.at/) (FIG. 1). The inventor had previously established that interaction between CD133 and the aptamer occurs via the loop of the aptamer (Shigdar S et al (2013) Cancer Letters 330:84-95). Furthermore, doxorubicin (DOX) is known to intercalate into G-C base pairing in DNA (FIG. 1B). Therefore, the RNA stem in the CD133 aptamer was replaced with a 10-bp DNA stem to provide a platform for DOX loading. In order to increase the stability of both the target-binding part of the aptamer and the DOX-DNA conjugate, a 5'methyl-dC in the DNA stem, was used, providing a stronger base-pairing than its native counterpart.

Figure 2:
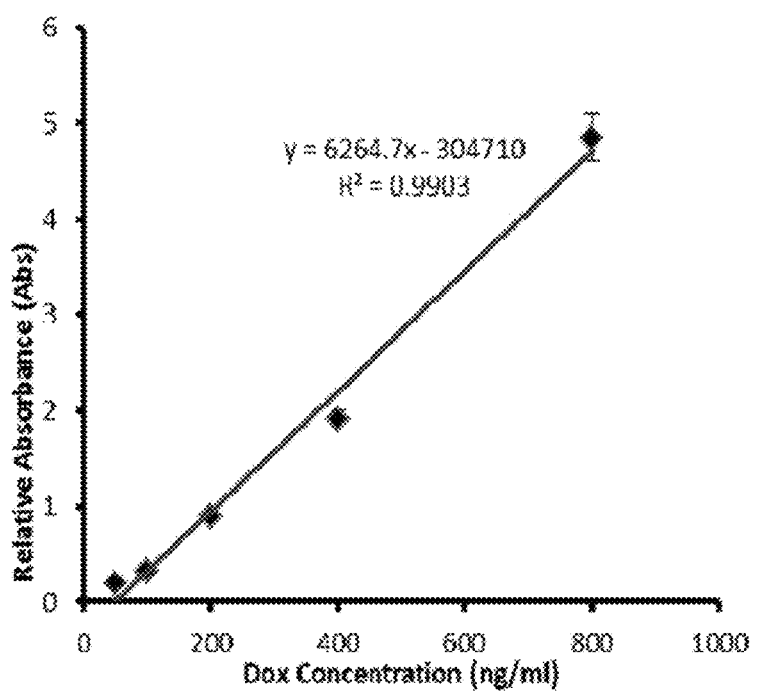
FIG. 2. Schematic diagram of the predicted intercalation of DOX to CD133 RNA-DNA hybrid aptamer. (A) The secondary structure of the aptamer (left) determined via VIENNA software and the molecule structure of doxorubicin (right). (B) Representation of possible intercalation between the aptamer and DOX due to the drugs high affinity for double stranded G-C pairing.
Figure 3:
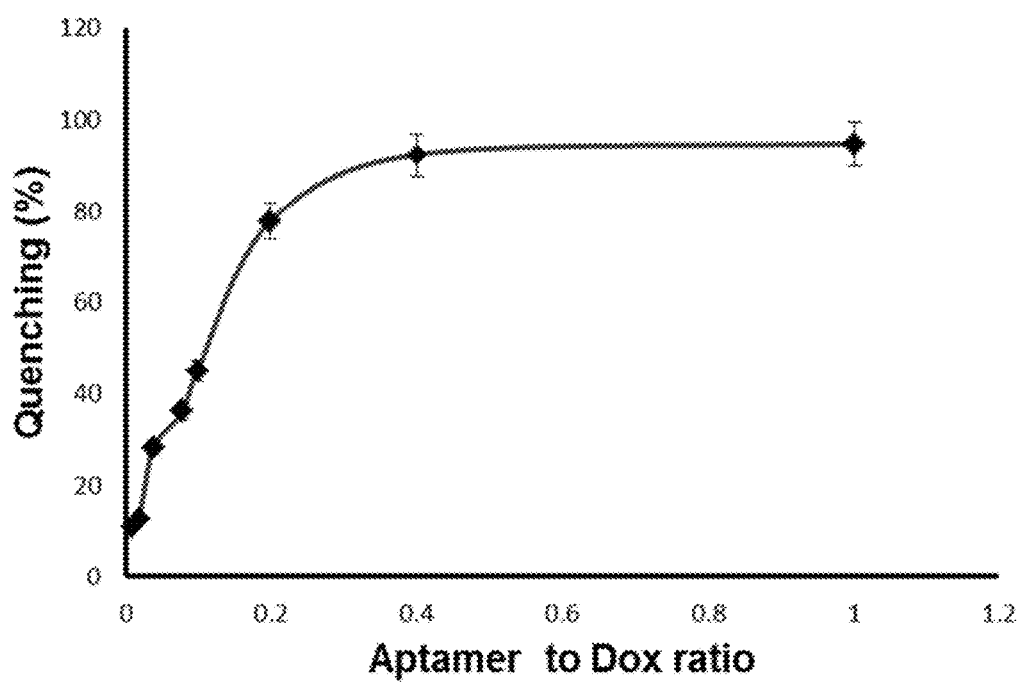
FIG. 3. To determine the relationship between fluorescence intensity and the DOX concentration. Various concentrations of DOX were used to measure the fluorescence intensity. Data shown are mean±SE, n=3.

The optimal molar ratio for DOX loading in the aptamer was determined by a conjugation assay with sequential increases of aptamer to DOX molar ratio. To perform this semi-quantitative analysis, a quantitative assessment of DOX fluorescence at various concentrations was first determined using UV-Spec and HPLC (FIG. 2). This provides a correlation between the fluorescent intensity measured and the actual concentration of free DOX. The intercalation of DOX into the CD133 aptamer was monitored via UV-Spec and high performance liquid chromatography (HPLC). FIG. 3 shows the DOX's natural fluorescence and subsequent maximum quenching upon intercalation with a molar ratio of CD133 aptamer to DOX being 0.4:1. The loading of DOX to aptamer increased with increasing concentrations of aptamer used and reached a plateau at 0.4. This data, along with the baseline of free DOX within a standard curve, allowed the monitoring of the conjugation of DOX to aptamer as percentage of quenching (FIG. 3).

Example 2

The In Vitro Stability of the DOX-Aptamer Conjugates

Figure 4:
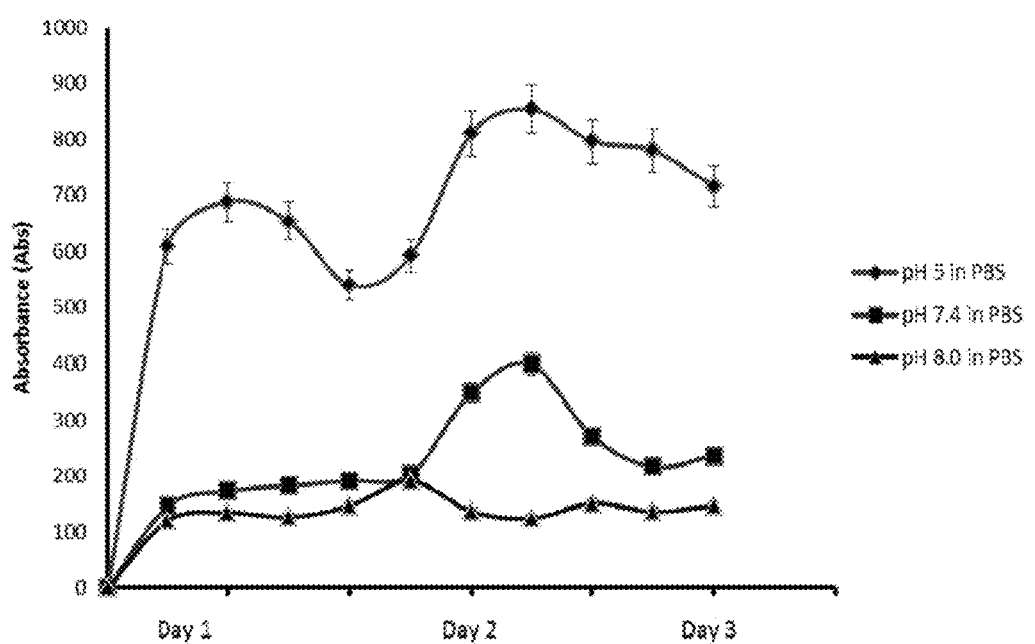
FIG. 4. Fluorescence quenching curve after intercalation of DOX into CD133 aptamer. After conjugation, the aptamer-Dox conjugate was purified. The fluorescence of DOX was determined via UV absorption at a wavelength of 495 nm. Data shown are mean±SE, n=3.
Figure 5:
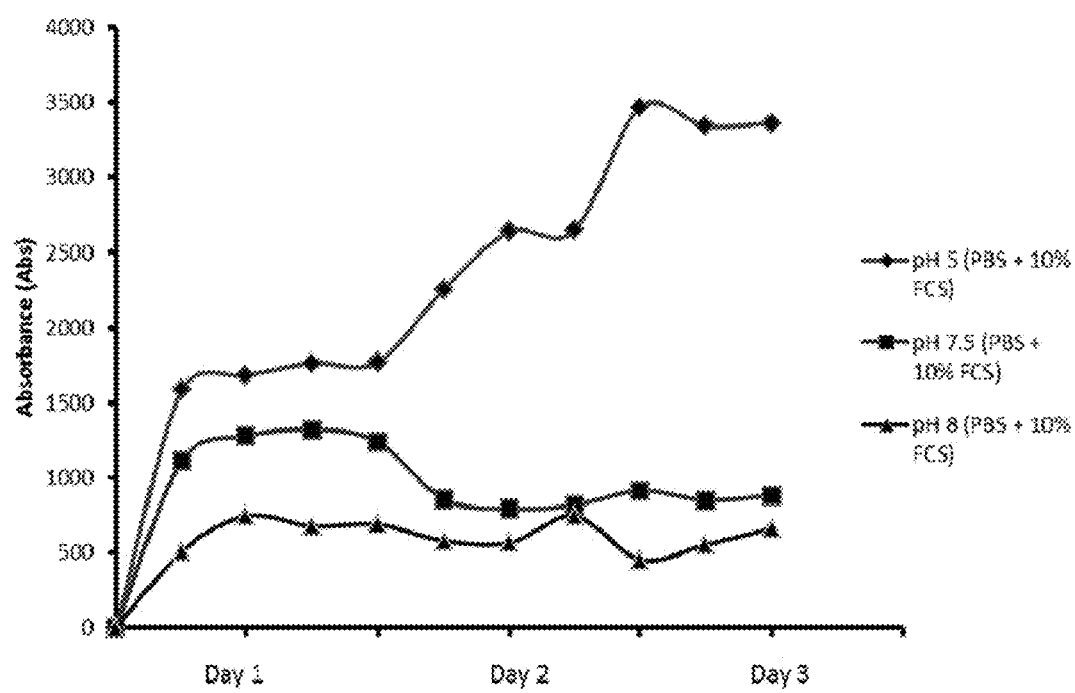
FIG. 5. DOX release from conjugate over three days in PBS. The absorbance (Y-axis) correlates to the DOX fluorescent intensity within the dialysis cassette. The greater the intensity the more DOX that has been released from the conjugate. Data shown are mean±SE, n=3.

Controlled and sustained drug release is important for drug delivery systems. The inventor has previously shown that aptamers are internalized via endocytosis, possibly into the endosome and lysosome compartments that have a pH of 6.0 to 5.0 9 Shigdar S et al (2011) Cancer science 102:991-998. Therefore, the in vitro release profile of DOX from the aptamer-Dox conjugate in a pH range was investigated in PBS and PBS with foetal calf serum (FCS). As shown in FIGS. 4 and 5, the in vitro DOX release from aptamer-Dox was pH-dependent and exhibited a steadily continued release pattern with a little initial burst release. At pH 7.4 (the physiological pH found in the circulation system), minimal release of the intercalated DOX from the aptamer detected after 48 h in PBS. Similarly, DOX release from aptamer-Dox was much lower at pH 8.0. However, at a pH 5.0, the release of DOX increased dramatically in PBS. In order to mimic the conditions in circulation, the DOX release was measured in PBS supplemented with FCS (FIG. 5) and found to be consistent with FIG. 4, regarding DOX release over different pH. Such a pH-dependent release behaviour is desirable as the DOX should remain conjugated with the aptamer in the neutral environment of systemic circulation in vivo and be released in the acidic environment of the late endosome/lysosome after internalisation into the tumour cells.

Example 3

Determination of the Equilibrium Dissociation Constant of Aptamer Conjugates

Figure 6:
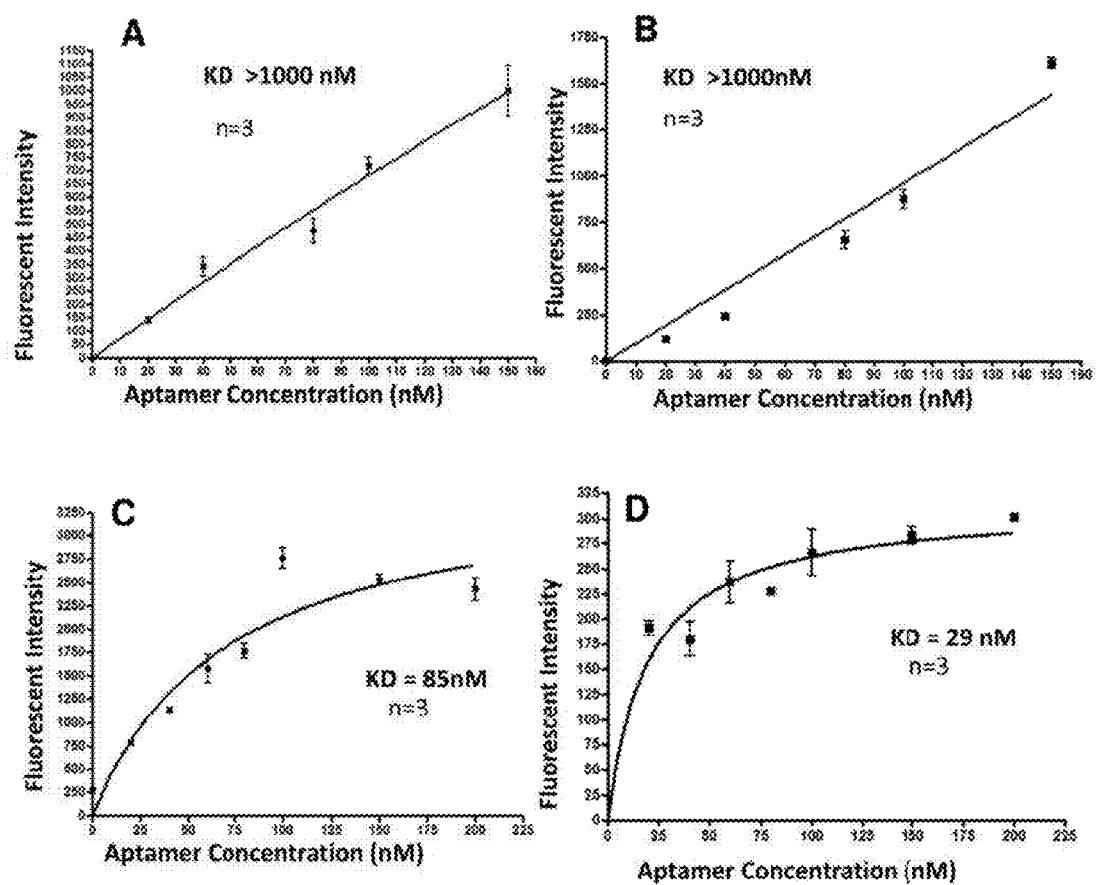
FIG. 6. Determination of dissociation constant for CD133 aptamer-Dox conjugates in CD133 negative HEK2932 and CD133 positive HT29 cells. The binding was studied using a fluorescently labelled CD133 Aptamer and CD133 Aptamer-Dox conjugates with concentrations ranging from 0-200 nM. (A) HEK293T cell line treated with positive CD133 Aptamer-Dox conjugate, (B) HEK2932 treated with negative control Aptamer-Dox conjugated (C) HT29 treated with positive CD133 Aptamer (unconjugated) and (D) HT29 cells treated with positive CD133 Aptamer-Dox conjugated. Data shown are mean±SE, n=3.
Figure 7:
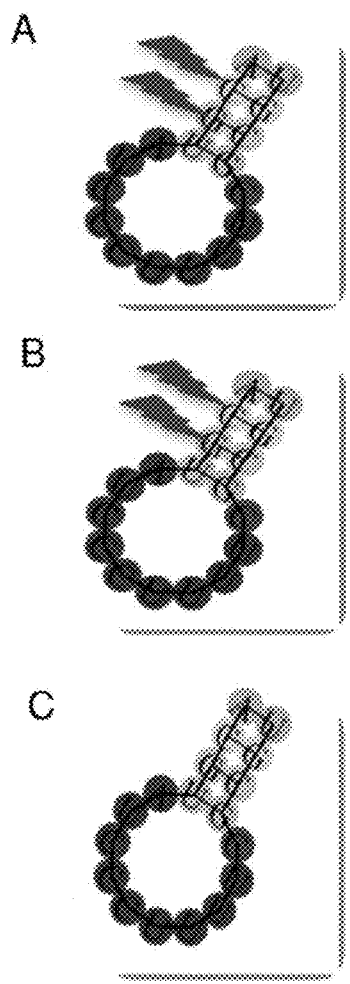
FIG. 7. CD133 aptamers used for determination of dissociation constant for CD133 aptamer-Dox conjugates. (A)

To determine whether the conjugation of DOX impedes binding affinity and specificity of the aptamer to CD133 the fluorescently labelled Cy5 aptamer-Dox conjugate was incubated with HT29 colorectal cancer cells and the equilibrium dissociation constant ($K_D$) was determined via flow cytometric analysis (FIG. 6). CD133 aptamers used in the study of the dissociation constant are presented in FIG. 7.

Two cell lines, HT29 and HEK293T, were chosen for the study. HT29 expresses high levels of CD133, whereas HEK293 cell line does not express CD133 and was used as a negative control for the specificity of CD133 binding. As shown in FIG. 6A, the aptamer-Dox conjugate had negligible affinity to the negative control cells (HEK293T) since it displayed a $K_D$ of >1000 nM. To ascertain that CD133 aptamer binds to CD133 via specific molecular interaction rather than a non-specific binding between a nucleic acid and CD133, the experiments were repeated with a negative control aptamer-Dox conjugate (FIG. 6B). This negative control aptamer has the identical nucleic acid sequence as the positive aptamer with the exception of a 2'-O-methyl modification instead of a 2'-fluoro chemical modification.

Therefore, it has an altered 3-D structure that abolishes its binding to CD133. The negative-control aptamer-Dox also showed no binding to the HT29 cell line with an equilibrium dissociation of $K_D$>1000 nM. In contrast, the CD133 aptamer (FIG. 6C) and CD133 aptamer-Dox conjugate (FIG. 6D) bound HT29 cells with high affinity at 84.81 nM and 23.89 nM respectively, suggesting both a retention in affinity and improvement of affinity with DOX intercalated into the stem.

Example 4

Cellular Internalisation of the Aptamer-Dox Conjugate

The elevated expression of ABC transporters present on the plasma membrane that efflux free drugs that passively diffuse into the cells is one of the key mechanisms underlying chemoresistance in CSCs. One way to overcome such defences is to deliver the cytotoxic drugs via endocytosis, thus bypassing the plasma membrane-based drug efflux pumps. To assess the ability of the CD133 aptamer-Dox conjugate to efficiently deliver the drug intracellularly, the internalisation of the conjugate was analysed qualitatively via confocal microscopy (FIG. 8). Aptamer and DOX treatments used for the assessment of internalization are presented in FIG. 9.

The excitation and emission wavelength of DOX is 480 and 580 nm respectively, while the aptamer was labelled with Cy5 with an emission and excitation wavelength of 645/664 nm. This was so that DOX and aptamer within the conjugate could be clearly identified via different fluorescent channels for confocal flow cytometric analyses. HT29 cells were first incubated with CD133 aptamer labelled with Cy5 and shown to be successfully internalised after 1 hour incubation (FIG. 8A). Next, to determine whether the intercalation of DOX could affect internalisation the experiment was repeated with aptamer-Dox conjugate (FIG. 8B). As shown in FIGS. 8A & B, the conjugate displayed a similar level of internalisation to its CD133 aptamer-only counterpart. A negative control aptamer and cell line (293T) also confirmed specificity of conjugate similar to affinity results (FIG. 8C-D.) Furthermore, the level of intracellular fluorescence for DOX measured using the TRITC channel was much higher, compared to that for free DOX shown in FIG. 8E.

Example 5

Establishment of the Capability of Aptamer-Dox Conjugate in Eliminating Self-Renewal Cells In Vitro Functional capacity, not phenotype expression, is critical for analysing CSCs. This is because, while the characteristics of CSCs may vary dependent on cancer type, stage of tumour growth and heterogeneity within a population, its capacity to self-renew and generate entire progenies of cells remains (Kreso A and O'Brien C A in Current Protocols in Stem Cell Biology (John Wiley and Sons, Inc., 2007). By conditioning cells under conditions that promote self-renewal (a key property of CSCs) and eliminating terminally differentiated cells, the formation of tumourspheres in vitro is a good indicator of self-renewal potential (Kreso et al supra). Previous studies have established that DOX is ineffective at killing CSCs (Zeppernick F et al (2008) Clin Cancer Res 14:123-129, Zhuang X et al (2012) BMC Cancer 12:1-16). To evaluate if the CD133 aptamer conjugate could improve DOX's cytotoxic capacity against CSCs, a tumoursphere formation assay was executed as described above. To analyse the differences in CSC targeting between the conventional drug DOX and the newly developed aptamer-Dox conjugates, concentrations of DOX based on published IC50 values were used (Poljakova J et al (2008) Interdisciplinary toxicology 1:186-189; Shen F et al (2008) The Journal of pharmacology and experimental therapeutics 324:95-102; Oudard S et al (1991) Cancer chemotherapy and pharmacology 28:259-265). To this end, various concentrations of HT29 cells were seeded in ultra-low attachment plates. For 96-well ultra-low attachment plates, cells were seeded at a serial dilution of density, from 500/well, 200/well, 100/well, 50/well, 10/well and 5/well. For 6-well ultra-low attachment plates, cells were seeded at a density of wither 2000/well, or 4000/well. Cells were incubated with either 1, 1.5, or 2 µM of free DOX or equivalent concentration of Aptamer-Dox. Three days later, the size of the tumourspheres (FIG. 10) and the number of wells forming tumourspheres (FIG. 11) were assessed. Although there was no obvious inhibition of sphere formation at higher cell seeding dose (FIG. 11), there was a significant decrease in tumoursphere size between cells treated with Aptamer-Dox and control as well as free DOX (FIG. 10).

To obtain a true efficacy of aptamer-Dox conjugate in vitro, lower seeding dose of cells (10 or 5 cells/well) were used (FIG. 11). Cells treated with free DOX showed no significant decrease in the frequency of tumoursphere formation, except for those with a cell seeding dose of 5 cells/well or less. In contrast, cells treated with aptamer-Dox conjugate showed a considerable decrease in the frequency of tumoursphere formation compared to PBS control and free DOX. To further confirm the results obtained with 96-well ultralow adherent plates, a second (6-well) version of the tumoursphere assay was used to ensure the results obtained were reproducible (FIG. 12). The difference in experimentation between the 96- to 6-well assays is that the latter allows for the formation of numerous tumourspheres compared to a single tumoursphere in the former. Similar to 96 well plate conditions, there was a dramatic decrease in tumoursphere formation in 6-well treated with aptamer-Dox compared to that treated with free DOX or control.

The invention claimed is:

1. An aptamer comprising the sequence 5'-X-ACGUAUACUAU-Y-3' (SEQ ID NO:1), wherein:
    the sequence of X and Y are complementary so as to be capable of base pairing;
    X and Y individually comprise a length of at least 10 alternating CG paired nucleotides sufficient to permit intercalation of at least one moiety thereto; and
    the aptamer specifically binds to CD133.

2. The aptamer of claim 1 wherein X and Y individually comprise:
    at least 12 CG paired nucleotides; or
    at least 14 CG paired nucleotides.

3. The aptamer of claim 1 which exhibits a dissociation constant (KD) for CD133 of about 24 nM or less.

4. The aptamer of claim 1, comprising the sequence 5'-CGCGCGCCGCACGUAUACUAUGCGGCGCGCG-3' (SEQ ID NO:2).

5. The aptamer of claim 4, wherein the aptamer:
    consists essentially of the sequence of SEQ ID NO:2; or
    consists of the sequence of SEQ ID NO:2.

6. The aptamer of claim 1, wherein the moiety is a DNA stain or molecule used in chemotherapeutic treatment.

7. The aptamer of claim 6 wherein the moiety is doxorubicin.

8. The aptamer of claim 1 comprising one or more modifications that increase aptamer stability.

9. The aptamer of claim 8, wherein:
    the pyrimidine nucleotide bases (C and/or U) in the loop region of the aptamer are 2'-fluoro (2'-F) modified;
    the 3' end is coupled to a phosphate group, a phosphate ester, or an inverted dT ((invdT-3'); and/or
    the 5' end is coupled to a dye.

10. The aptamer of claim 1, comprising the sequence 5'-X-A(2'fC)G(2'-fU)A(2'fU)A(2'fC)(2'fU)A(2'fU)-Y-(inv dT)-3' (SEQ ID NO:4) wherein X and Y are complementary so as to be capable of base pairing and wherein X and Y individually comprise a length of at least 10 alternating CG paired nucleotides wherein C is 5-methyl dC, f=2-fluoro and inv dT=an inverted dT and wherein the length of X and Y is sufficient to permit intercalation of at least one moiety thereto.

11. The aptamer of claim 10, comprising the sequence 5'-mCGmCGmCGmCmCGmCA(2'fC)G(2'-fU)A(2'fU)A(2'fC)(2'fU)A(2'fU)GmCGGmCGmCGmCG-(inv dT)-3' (SEQ ID NO:5), wherein C=5-methyl dC, f=2-fluoro and inv dT=an inverted dT.

12. An aptamer having substantially the same ability to bind to CD133 by exhibiting a dissociation constant (KD) for CD133 of about 24 nM or less as that of an aptamer comprising the sequence of SEQ ID NO:2, SEQ ID NO:4 or SEQ ID NO:5, wherein the aptamer comprises a length of at least 10 alternating CG paired nucleotides.

13. The aptamer of claim 1 which specifically binds to CD133+ cancer stem cells(s).

14. A diagnostic or theranostic agent comprising the aptamer of claim 1.

15. A method for identifying a CD133 expressing cell(s) and/or a CD133+ cancer stem cell(s) in a subject or a biological sample obtained from a subject, having, or suspected of having cancer, comprising contacting the cell(s) and/or the cancer stem cell(s) with the diagnostic or theranostic agent of claim 14.

16. The aptamer of claim 1 further coupled to an active moiety.

17. A method of treating cancer comprising CD133+ cells in a subject in need thereof, comprising providing the subject with the aptamer of claim 1.

18. A composition comprising a therapeutically effective amount of the aptamer of claim 1 and a pharmaceutically acceptable carrier and/or excipient.

19. A method of treating cancer comprising CD133+ cells in a subject in need thereof, comprising providing the subject with the diagnostic or theranostic agent of claim 14.

20. A composition comprising a therapeutically effective amount of the diagnostic or theranostic agent of claim 14 and a pharmaceutically acceptable carrier and/or excipient.

* * * * *

SEQUENCE LISTING

<160> NUMBER OF SEQ ID NOS: 5

<210> SEQ ID NO 1
<211> LENGTH: 11
<212> TYPE: RNA
<213> ORGANISM: Artificial Sequence
<220> FEATURE:
<223> OTHER INFORMATION: a synthetic aptamer against CD133

<400> SEQUENCE: 1
acguauacua u                                                          11

<210> SEQ ID NO 2
<211> LENGTH: 31
<212> TYPE: RNA
<213> ORGANISM: Artificial Sequence
<220> FEATURE:
<223> OTHER INFORMATION: RNA aptamer

<400> SEQUENCE: 2
cgcgcgccgc acguauacua ugcggcgcgc g                                    31

<210> SEQ ID NO 3
<211> LENGTH: 11
<212> TYPE: RNA
<213> ORGANISM: Artificial Sequence
<220> FEATURE:

```
<223> OTHER INFORMATION: a synthetic aptamer against CD133

<400> SEQUENCE: 3
acguauacua u                                                                11

<210> SEQ ID NO 4
<211> LENGTH: 14
<212> TYPE: DNA
<213> ORGANISM: Artificial Sequence
<220> FEATURE:
<223> OTHER INFORMATION: a synthetic aptamer against CD133
<220> FEATURE:
<221> NAME/KEY: modified_base
<222> LOCATION: (3)..(3)
<223> OTHER INFORMATION: 2'-fluoro 5-methyl deoxycytidine
<220> FEATURE:
<221> NAME/KEY: modified_base
<222> LOCATION: (5)..(5)
<223> OTHER INFORMATION: 2'-fluoro deoxyuridine
<220> FEATURE:
<221> NAME/KEY: modified_base
<222> LOCATION: (7)..(7)
<223> OTHER INFORMATION: 2'-fluoro deoxyuridine
<220> FEATURE:
<221> NAME/KEY: modified_base
<222> LOCATION: (9)..(9)
<223> OTHER INFORMATION: 2'-fluoro 5-methyl deoxycytidine
<220> FEATURE:
<221> NAME/KEY: modified_base
<222> LOCATION: (10)..(10)
<223> OTHER INFORMATION: 2'-fluoro deoxyuridine
<220> FEATURE:
<221> NAME/KEY: modified_base
<222> LOCATION: (12)..(12)
<223> OTHER INFORMATION: 2'-fluoro deoxyuridine
<220> FEATURE:
<221> NAME/KEY: modified_base
<222> LOCATION: (14)..(14)
<223> OTHER INFORMATION: inverted deoxythymidine (reverse linkage)

<400> SEQUENCE: 4
sacguauacu aust                                                             14

<210> SEQ ID NO 5
<211> LENGTH: 32
<212> TYPE: DNA
<213> ORGANISM: Artificial Sequence
<220> FEATURE:
<223> OTHER INFORMATION: a synthetic aptamer against CD133
<220> FEATURE:
<221> NAME/KEY: modified_base
<222> LOCATION: (1)..(1)
<223> OTHER INFORMATION: 5-methyl deoxycytidine
<220> FEATURE:
<221> NAME/KEY: modified_base
<222> LOCATION: (3)..(3)
<223> OTHER INFORMATION: 5-methyl deoxycytidine
<220> FEATURE:
<221> NAME/KEY: modified_base
<222> LOCATION: (5)..(5)
<223> OTHER INFORMATION: 5-methyl deoxycytidine
<220> FEATURE:
<221> NAME/KEY: modified_base
<222> LOCATION: (7)..(8)
<223> OTHER INFORMATION: 5-methyl deoxycytidine
<220> FEATURE:
<221> NAME/KEY: modified_base
<222> LOCATION: (10)..(10)
<223> OTHER INFORMATION: 5-methyl deoxycytidine
<220> FEATURE:
<221> NAME/KEY: modified_base
<222> LOCATION: (12)..(12)
<223> OTHER INFORMATION: 2'-fluoro 5-methyl deoxycytidine
<220> FEATURE:
<221> NAME/KEY: modified_base
```

```
<222> LOCATION: (14)..(14)
<223> OTHER INFORMATION: 2'-fluoro deoxyuridine
<220> FEATURE:
<221> NAME/KEY: modified_base
<222> LOCATION: (16)..(16)
<223> OTHER INFORMATION: 2'-fluoro deoxyuridine
<220> FEATURE:
<221> NAME/KEY: modified_base
<222> LOCATION: (18)..(18)
<223> OTHER INFORMATION: 2'-fluoro 5-methyl deoxycytidine
<220> FEATURE:
<221> NAME/KEY: modified_base
<222> LOCATION: (19)..(19)
<223> OTHER INFORMATION: 2'-fluoro deoxyuridine
<220> FEATURE:
<221> NAME/KEY: modified_base
<222> LOCATION: (21)..(21)
<223> OTHER INFORMATION: 2'-fluoro deoxyuridine
<220> FEATURE:
<221> NAME/KEY: modified_base
<222> LOCATION: (23)..(23)
<223> OTHER INFORMATION: 5-methyl deoxycytidine
<220> FEATURE:
<221> NAME/KEY: modified_base
<222> LOCATION: (26)..(26)
<223> OTHER INFORMATION: 5-methyl deoxycytidine
<220> FEATURE:
<221> NAME/KEY: modified_base
<222> LOCATION: (28)..(28)
<223> OTHER INFORMATION: 5-methyl deoxycytidine
<220> FEATURE:
<221> NAME/KEY: modified_base
<222> LOCATION: (30)..(30)
<223> OTHER INFORMATION: 5-methyl deoxycytidine
<220> FEATURE:
<221> NAME/KEY: modified_base
<222> LOCATION: (32)..(32)
<223> OTHER INFORMATION: inverted deoxythymidine (reverse linkage)

<400> SEQUENCE: 5
cgcgcgccgc acguauacua ugcggcgcgc gt                                     32
```